(12) United States Patent
Kim et al.

(10) Patent No.: US 12,076,530 B2
(45) Date of Patent: Sep. 3, 2024

(54) APPARATUS FOR PREVENTING BACKFLOW

(71) Applicant: ENGAIN, Seongnam-si (KR)

(72) Inventors: Dong Chul Kim, Suwon-si (KR); Young Gook Koh, Seongnam-si (KR); Se Yun Jeong, Yongin-si (KR)

(73) Assignee: ENGAIN, Seongnam-si (KR)

( * ) Notice: Subject to any disclaimer, the term of this patent is extended or adjusted under 35 U.S.C. 154(b) by 883 days.

(21) Appl. No.: 17/028,339

(22) Filed: Sep. 22, 2020

(65) Prior Publication Data

US 2021/0093780 A1 Apr. 1, 2021

(30) Foreign Application Priority Data

Sep. 27, 2019 (KR) .................. 10-2019-0119311
Apr. 8, 2020 (KR) .................. 10-2020-0042747

(51) Int. Cl.
*A61M 5/168* (2006.01)
*A61M 5/14* (2006.01)
(Continued)

(52) U.S. Cl.
CPC .. *A61M 5/16881* (2013.01); *A61M 2005/1406* (2013.01); *A61M 2039/2406* (2013.01);
(Continued)

(58) Field of Classification Search
CPC ...... A61M 5/16881; A61M 2005/1406; A61M 2039/244; A61M 2039/2406;
(Continued)

(56) References Cited

U.S. PATENT DOCUMENTS 2,867,213 A 1/1959 Thomas
3,191,600 A * 6/1965 Everett ............... A61M 1/3627
604/323

(Continued)

FOREIGN PATENT DOCUMENTS

EP 0 737 483 A1 10/1996
JP 4339682 B2 10/2009
(Continued)

OTHER PUBLICATIONS

An Office Action mailed by China National Intellectual Property Administration on Mar. 30, 2022, which corresponds to Chinese Application No. 202011027606.6 and is related to U.S. Appl. No. 17/028,339; with English language translation.
(Continued)

*Primary Examiner* — Nilay J Shah
(74) *Attorney, Agent, or Firm* — Studebaker & Brackett PC

(57) ABSTRACT

An apparatus for preventing backflow. The apparatus includes a housing; a trap flow part forming a flow passage for a medical fluid, a discharge part provided on an lower portion of the housing and to receive the medical fluid from the trap flow part and to discharge the medical fluid; a backflow prevention chamber part provided between the trap flow part and the discharge part; and a plate-shaped backflow prevention member provided on one surface of the inner side of the backflow prevention chamber part connected to the trap flow part and in close contact with a periphery of the outlet opening, the plate-shaped backflow prevention member being provided to open or close the opening depending on forward flow and the backflow of the medical fluid.

8 Claims, 24 Drawing Sheets

(51) Int. Cl.
  *A61M 39/24* (2006.01)
  *F16K 3/04* (2006.01)
  *F16K 15/03* (2006.01)

(52) U.S. Cl.
  CPC .......... *A61M 2039/244* (2013.01); *F16K 3/04* (2013.01); *F16K 15/03* (2013.01)

(58) Field of Classification Search
  CPC .......... A61M 39/24; A61M 2039/2473; F16K 15/03; F16K 15/031; F16K 31/521; F16K 31/52408; F16K 31/52441; F16K 31/5282; F16K 3/04; F16K 3/00; B65D 90/582; B65D 90/585
  See application file for complete search history.

(56) References Cited

U.S. PATENT DOCUMENTS

| | | | | |
|---|---|---|---|---|
| 3,348,569 A | * | 10/1967 | Frye | .................... F16K 15/1848 137/269.5 |
| 2008/0308159 A1 | * | 12/2008 | Stunkard | ............. F16K 27/0209 137/315.33 |
| 2011/0034907 A1 | * | 2/2011 | Kaern | .................... F16K 15/16 604/323 |
| 2014/0066849 A1 | | 3/2014 | Ki | |
| 2016/0354595 A1 | | 12/2016 | Gallagher | |

FOREIGN PATENT DOCUMENTS

| | | |
|---|---|---|
| KR | 20-1997-056956 U | 11/1997 |
| KR | 20-2019-0001420 U | 6/2019 |

OTHER PUBLICATIONS

Office Action issued in KR 10-2019-0119311; mailed by the Korean Intellectual Property Office on Feb. 14, 2020.

Office Action issued in KR 10-2020-0042747; mailed by the Korean Intellectual Property Office on Sep. 4, 2020.

The partial European search report (R. 64 EPC) issued by the European Patent Office on Jan. 26, 2021, which corresponds to European Patent Application No. 20197650.3-1122 and is related to U.S. Appl. No. 17/028,339.

The extended European search report issued by the European Patent Office on Jun. 11, 2021, which corresponds to European Patent Application No. 20197650.3-1122 and is related to U.S. Appl. No. 17/028,339.

* cited by examiner

APPARATUS FOR PREVENTING BACKFLOW

CROSS-REFERENCE TO RELATED APPLICATION

This application claims priority from Korean Patent Application Nos. 10-2019-0119311 filed on Sep. 27, 2019 and 10-2020-0042747 filed on Apr. 8, 2020 in the Korean Intellectual Property Office, and all the benefits accruing therefrom under 35 U.S.C. 119, the contents of which in their entirety are herein incorporated by reference.

BACKGROUND

1. Technical Field

The present invention relates to an apparatus for preventing backflow, and more specifically, to an apparatus for preventing backflow that may prevent blood from flowing back in the course of supplying while supplying a liquid medicine or medical fluid to a body smoothly.

2. Description of the Related Art

Generally, a fluid set refers to a medical product used for injecting a fluid or a liquid medicine into a human body for medical purposes. The fluid set is used for intravenous injection.

The general form of the infusion set consists of a chamber coupled to a pharmaceutical container, a regulator, a hub coupled to a venous catheter, and a tube to connect the chamber to the hub. In addition, the infusion of the fluid by the fluid set is performed by a method of inserting the intravenous catheter into a blood vessel and connecting the hub of the intravenous catheter with the fluid set.

A conventional venous catheter is made of a flexible material to protect blood vessels, and is used as a unit with a metal guide needle to facilitate blood vessel entry. When the guide needle and the intravenous catheter are configured as a unit, the guide needle penetrates a skin and serves to guide the vascular entry of the venous catheter, and then is separated from the venous catheter and discarded. The intravenous catheter acts to supply the fluid into the blood vessel by connecting the fluid set to the hub while entering the blood vessel.

A control unit may implement a function of adjusting the dosage of the fluid when the fluid of the fluid set is supplied through the hub while the intravenous catheter is entered into a porch of a patient. The control unit may be provided in the intravenous catheter or may be provided in a predetermined position of the hub.

In conventional injection needles for fluid injection, when a position of the fluid injector is significantly lower than that of the patient's body during injection, or when a position of the patient's heart is higher than that of the fluid injector due to the patient's movement, the pressure in blood vessels increases. Therefore, the pressure of the blood vessel is relatively higher than the pressure of the fluid injected into the blood vessel. As a result, a problem may arise in which the fluid is pushed out and blood flows out of the patient's body through the intravenous catheter.

The backward flowed blood mixes with the fluid, and platelet necrosis begins immediately. The necrotic platelets may eventually block the intravenous catheter, which may cause difficulty in injecting the fluid.

Therefore, there is a need for an apparatus for preventing backflow that may prevent blood from flowing back in the course of supplying while supplying a liquid medicine or fluid to a body smoothly.

SUMMARY

Aspects of the present invention provide an apparatus for preventing backflow, in which the apparatus is provided in a venous catheters or a hub, and may stably carry a forward movement of a fluid, while blocking the movement in a reverse direction.

However, aspects of the present invention are not restricted to those set forth herein. The above and other aspects of the present invention will become more apparent to one of ordinary skill in the art to which the present invention pertains by referencing the detailed description of the present invention given below.

According to an aspect of an exemplary embodiment, there is provided an apparatus for preventing backflow, comprising: a housing; a trap flow part provided on an inner side of the housing, the trap flow part forming a flow passage for a medical fluid, wherein the flow passage is formed to be bent at adjacent portions of one side and the other side of a body, wherein at least one outlet opening is formed at an end of trap flow part; a discharge part provided on an lower portion of the housing and to receive the medical fluid from the trap flow part and to discharge the medical fluid; a backflow prevention chamber part provided between the trap flow part and the discharge part; and a plate-shaped backflow prevention member provided on one surface of the inner side of the backflow prevention chamber part connected to the trap flow part and in close contact with a periphery of the outlet opening, the plate-shaped backflow prevention member being provided to open or close the opening depending on forward flow and the backflow of the medical fluid.

The flow passage comprises: an inflow passage formed in a vertical direction in a center of the housing; a discharge passage formed in a vertical direction to be connected to the backflow prevention chamber in the center of the housing, and formed to be inclined toward the backflow prevention chamber; and a main flow passage provided to be connected between the inflow passage and the discharge passage, the main flow passage flowing the medical fluid while being bent at adjacent portions of one side and the other side of the housing, wherein a bottom surface connected to the discharge passage is formed to be inclined in a direction of the discharge passage.

An inlet opening connected to the outlet opening by inserting the outlet opening is formed on one surface of the backflow prevention chamber part, wherein an inner contact groove and an outer contact groove are formed on one surface of the backflow prevention chamber part, wherein the inner contact groove protrudes in a direction facing the trap flow part while forming a groove inward while surrounding the inlet opening, and wherein the outer contact groove protrudes stepwise between one surface of the backflow prevention chamber part and the inner contact groove around the inner contact groove, and wherein a contact inclined surface is provided on an upper portion of the other surface of the inner side of the backflow prevention chamber part, wherein the contact inclined surface is further away toward a lower portion, such that when the medical fluid flows forward, the contact inclined surface is in contact with the plate-shaped backflow prevention member, thereby limiting the bending of the plate-shaped backflow prevention member.

The backflow prevention member comprises: a support fixed to one surface of the inner side of the backflow prevention chamber part; and a sealing arranged above the support, the sealing being bent between one surface and the other surface of the inner side of the backflow prevention chamber according to a moving direction of the medical fluid around the support, and opening and closing the inlet opening while being close contact or releasing close contact around the inner contact groove and the outer contact groove.

The sealing comprises: a sealing plate extending to an upper portion of the support, the sealing plate being bent between one surface and the other surface of the inner side of the backflow prevention chamber part when the medical fluid flows forward and back, and wherein the sealing plate comprises a protruding surface that protrudes stepwise to a front of the sealing plate and engages with the outer contact groove to seal the inlet opening, and a contact protrusion that protrudes along an inner periphery of the protruding surface, engages with the inner contact groove, and forms a space in which the inlet opening is accommodated; and an opening and closing guide member provided on a rear surface of the sealing plate, wherein in a state where the sealing plate is bent due to the forward flow and the backflow of the medical fluid, the opening and closing guide member contacts the other surface of the inner side of the backflow prevention chamber part to limit movement of the sealing plate when the opening and closing guide member is pushed to the other surface of the inner side of the backflow prevention chamber part according to a pressure of the medical fluid flowing forward, or is pushed to one surface of the inner side of the backflow prevention chamber part by an inflow pressure of the medical fluid flowing back.

The opening and closing guide member comprises a guide body provided on the rear surface of the sealing plate, the guide body being formed from a top to a bottom in a center of the sealing plate, and formed in a semi-conical shape forming a hollow inward, wherein the guide body is in contact with the other surface of the inner side of the backflow prevention chamber part by bending movement of the sealing plate to limit the movement of the sealing plate, wherein un upper end of the guide body is provided with a control hole for adjusting the pressure of the medical fluid or blood flowing back into the hollow, and wherein the hollow pressurizes the sealing plate to be in close contact with one surface of the inner side of the backflow prevention chamber part while pushing up the guide body according to the inflow pressure of the medical fluid flowing back.

According to an aspect of an exemplary embodiment, there is provided another apparatus for preventing backflow, comprising: a first body comprising a hemispherical chamber with an opened surface and comprising a discharge passage in a lower portion of the chamber; a second body mounted on the opened surface of the first body, the second body comprising a seating part on one surface facing one surface of the first body and comprising an inflow passage connected to the seating part; and a disk-shaped backflow prevention member closely mounted to the seating part between the first body and the second body, the backflow prevention member opening or closing between the seating part and the chamber while moving about one end by a predetermined rotation according to the forward flow of the medical fluid flowing in the inflow passage and the backflow generated in the discharge passage.

The backflow prevention member comprises: a blocking body closely coupled to the seating part; a fixing protrusion part protruding from one side of the blocking body and rotatably seated and fixed between one surface of the first body and one surface of the second body; and a moving protrusion part protruding from the other side of the blocking body and provided between one surface of the first body and one surface of the second body, the moving protrusion part being guided to move in an up-and-down direction between the chamber and the seating part.

The seating part comprises: a seating groove in which the blocking body is seated in close contact, the seating groove having a diameter smaller than an upper portion of the chamber; a first extension groove extending in a first direction from one end of the seating groove toward an outer peripheral surface of the second body, and in which the fixing protrusion part is seated; and a second extension groove extending in a second direction opposite to the first direction from the other end of the seating groove, and in which the moving protrusion part is seated.

The first extension groove and the second extension groove extend stepwise from an end of the seating groove toward the first body, and wherein the second extension groove extends stepwise from the end of the seating groove toward the first body.

One surface of the blocking body is formed as a close contact surface that is in close contact with the seating groove, and wherein the other surface of the blocking body is formed as a pressing surface having a pressing groove that is in contact with the medical fluid flowing back.

The fixing protrusion part comprises: a first protrusion protruding from the blocking body in a first direction; and a rotating protrusion formed in a cylindrical shape in a vertical direction around the first protrusion in an end of the first protrusion.

The first extension groove comprises: an extension groove of the first protrusion extending in the first direction from the seating groove and in which the first protrusion is seated and is in close contacted; and an extension groove of the rotation protrusion extending in a direction perpendicular to the extension groove of the first protrusion, and in which the rotation protrusion is seated and rotatably fixed.

The moving protrusion part comprises: a second protrusion protruding from the blocking body in a second direction opposite to the first direction; and a guide hole formed at an end of the second protrusion and guiding up-and-down movement of the second protrusion.

The apparatus for preventing backflow, further comprising: a fixing part formed between the first body and the second body, the fixing part comprising a first fixing member positioned on one surface of the first body around the chamber and forming a semi-hollow-shaped second first groove and a second fixing member positioned in the extension groove of the rotation protrusion and forming a semi-hollow-shaped second groove corresponding to the semi-hollow-shaped first groove of the first fixing member, such that the fixing part rotatably fixes the fixing protrusion in a circular hollow formed by engaging the first groove and the second groove; and a moving guide formed between the first body and formed at a position facing the fixing part, the moving guide comprising a guide protrusion protruding from the second extension groove toward the chamber and a seating member protruding in a first direction into an inlet groove inserted to the other end of an inner peripheral surface of the chamber so as to guide up-and-down movement of the moving protrusion part, wherein a fastening hole into which an end of the guide protrusion is inserted is formed in the seating member.

According to an apparatus for preventing backflow in accordance with an embodiment of the present invention, when a medical fluid is introduced into a body, the medical fluid may be introduced at a constant rate by a trap flow part. In addition, even if backflow occurs between the trap flow part and a backflow prevention chamber part, it is not easy to move in a reverse direction due to a folded passage of the trap flow part, and thus there is a benefit of preventing backflow of blood.

Moreover, according to the apparatus for preventing backflow in accordance with the embodiment of the present invention, it is provided with a plate-shaped backflow prevention member capable of opening the connection of the trap flow part and the backflow prevention chamber part by pressure according to forward flow of a medical fluid while closing a connection path of the trap flow part and the backflow prevention chamber part. Therefore, there is a benefit of being able to block inflow of blood or the medical fluid into the trap flow part when backflow occurs.

According to the apparatus for preventing backflow in accordance with the embodiment of the present invention, it is provided with a disc-shaped backflow prevention member between a first body and a second body. Here, it is a simple structure in which the disk-shaped backflow prevention member is coupled according to a coupling of the first member and the second member. A seating groove may be opened by the movement of the backflow prevention member by the pressure according to the forward flow. When the backflow occurs, there is a benefit that the backflow prevention member closes the seating groove by the pressure according to the backflow to block the backflow of the medical fluid.

The effects of the present invention are not limited to the above-described effects and other effects which are not described herein will become apparent to those skilled in the art from the following description.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE EMBODIMENTS

Figure 1:
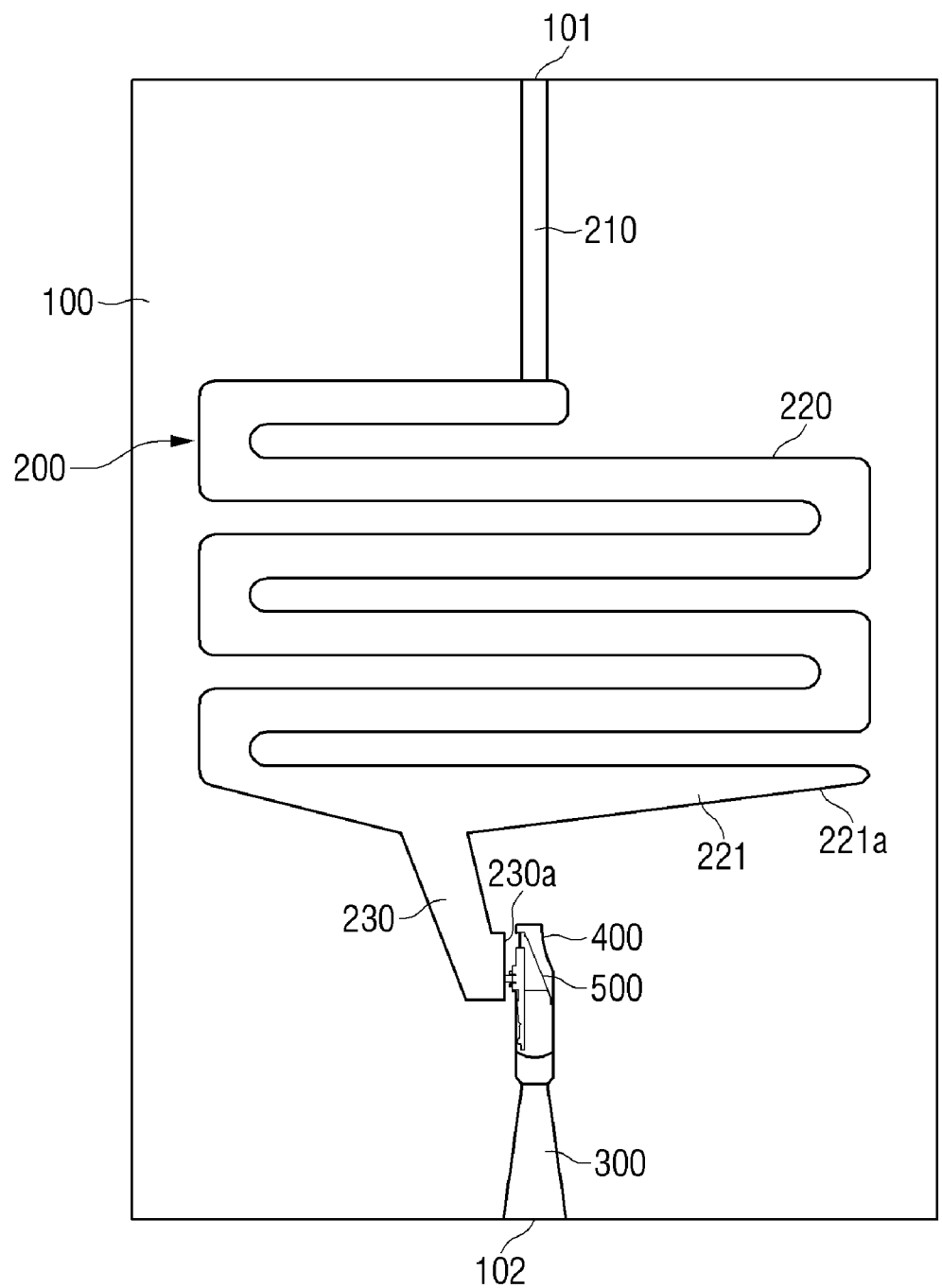
FIG. 1 is an internal cross-sectional view schematically showing the interior of an apparatus for preventing backflow according to an embodiment of the present invention.

Advantages and features of the disclosure and methods to achieve them will become apparent from the descriptions of exemplary embodiments herein below with reference to the accompanying drawings. However, the inventive concept is not limited to exemplary embodiments disclosed herein but may be implemented in various ways. The exemplary embodiments are provided for making the disclosure of the inventive concept thorough and for fully conveying the scope of the inventive concept to those skilled in the art. It is to be noted that the scope of the disclosure is defined only by the claims. Like reference numerals denote like elements throughout the descriptions.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

Terms used herein are for illustrating the embodiments rather than limiting the present disclosure. As used herein, the singular forms are intended to include plural forms as well, unless the context clearly indicates otherwise. Throughout this specification, the word "comprise" and variations such as "comprises" or "comprising," will be understood to imply the inclusion of stated elements but not the exclusion of any other elements.

Hereinafter, exemplary embodiments of the present disclosure will be described in detail with reference to the accompanying drawings.

Figure 2:
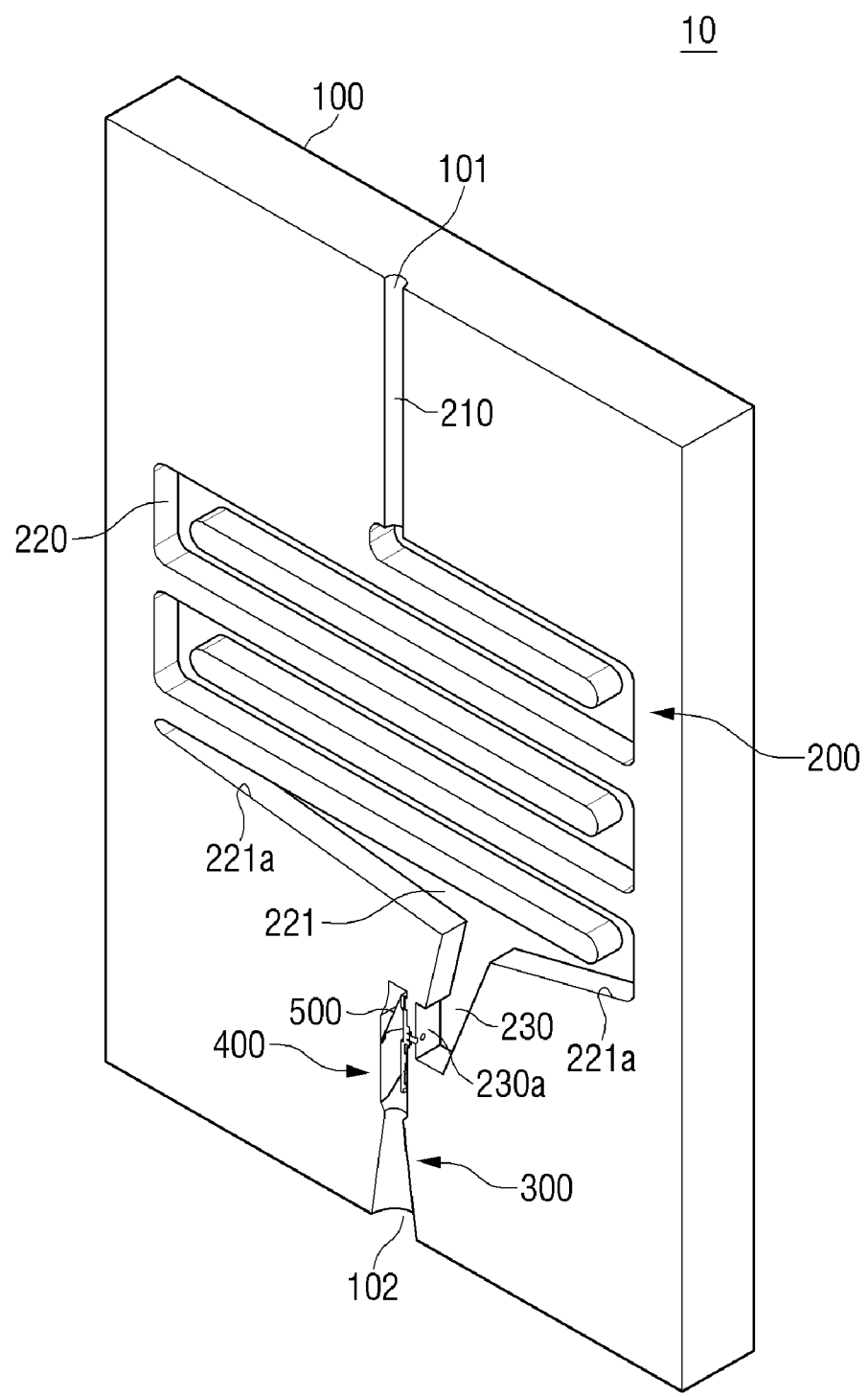
FIG. 2 is an internal cross-sectional perspective view in one direction schematically showing the interior of the apparatus for preventing the backflow according to the embodiment of the present invention.
Figure 3:
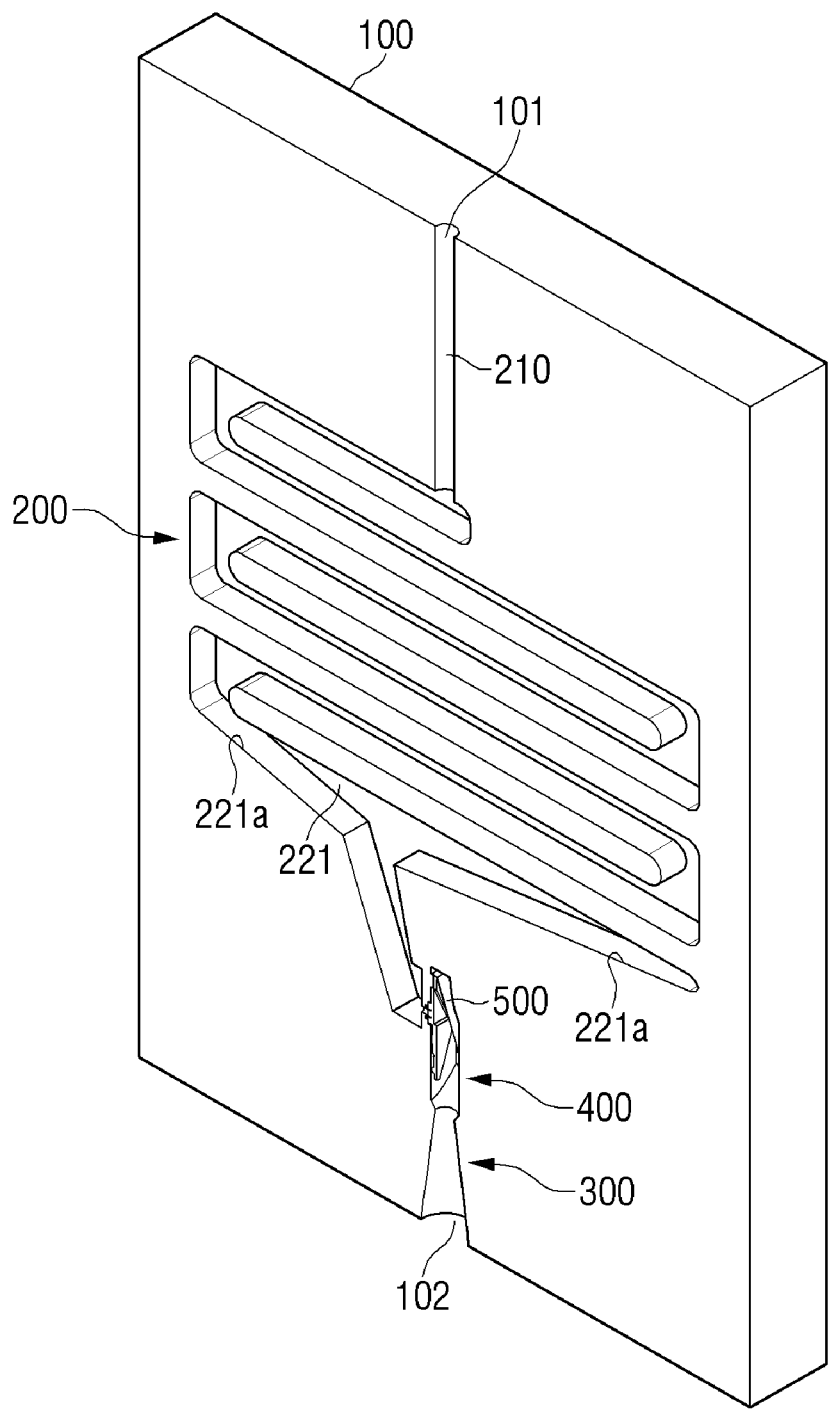
FIG. 3 is an internal cross-sectional perspective view in the other direction schematically showing the interior of the apparatus for preventing the backflow according to the embodiment of the present invention.

FIG. 1 is an internal cross-sectional view schematically showing the interior of an apparatus 10 for preventing backflow according to an embodiment of the present invention. FIG. 2 is an internal cross-sectional perspective view in one direction schematically showing the interior of the apparatus 10 for preventing the backflow according to the embodiment of the present invention. FIG. 3 is an internal cross-sectional perspective view in the other direction schematically showing the interior of the apparatus 10 for preventing the backflow according to the embodiment of the present invention.

Referring to FIGS. 1 to 3, the apparatus 10 for preventing the backflow according to the embodiment of the present invention may include a housing 100, a trap flow part 200, a discharge part 300, a backflow prevention chamber part 400, and a plate-shaped backflow prevention member 500.

The housing 100 has a rectangular shape, in which an upper portion of the housing 100 may be provided with an inlet 101 of a medical fluid into which the medical fluid is introduced, and an outlet 102 through which the medical fluid is discharged may be formed on a lower portion of the housing 100. A trip flow part connected to the inlet 101, a discharge part 300 for discharging the medical fluid, and the backflow prevention chamber part 400 between the trap flow part 200 and the discharge part 300 may be provided inside the housing 100.

The trap flow part 200 is provided inside the housing 100, and may be connected to the inlet 101 at the upper portion of the housing 100 to form a flow passage of the medical fluid from the top to the bottom of the housing 100. The trap flow part 200 according to the embodiment of the present invention may form a flow passage for the medical fluid, in which it may form a folded flow passage. In addition, at least one outlet opening 231 may be formed at an end of the trap flow part 200.

As described above, the trap flow part 200 forms a flow passage in a folded shape. To this end, the trap flow part 200 may include an inflow passage 210, a main flow passage 220, and a discharge passage 230.

The inflow passage 210 may be connected to the inlet 101 at the center of the housing 100 to form a hollow in the vertical direction.

The main flow passage 220 may be bent connected to an end of the inflow passage 210, and it may be provided to be bent at adjacent portions of one side and the other side of the housing 100 to receive the medical fluid moved in the inflow passage 210 and to flow the medical fluid. For example, the main flow passage 220 may be formed as a hollow that is bent in a '=' shape.

In addition, a flow passage positioned at the bottom of the main flow passage 220 (hereinafter referred to as "a bottom passage 221") may be connected to the discharge passage 230 to be described later. Specifically, the discharge passage 230 is connected in the vertical direction at the center portion of the bottom passage 221, in which a bottom surface 221a of the bottom passage 221 may be formed to be inclined in a direction of the discharge passage 230 so that the medical fluid introduced into the bottom passage 221 may be introduced into the discharge passage 230.

The discharge passage 230 is provided at an end of the main flow passage 220, and an end of the discharge passage 230 may form the outlet opening 231. The outlet opening 231 may be formed to face a horizontal direction in the discharge passage 230. It may be formed in the vertical direction in the bottom passage 221 to be connected to the backflow prevention chamber part 400 at the center of the housing 100. As described above, one end of the discharge passage 230 may be provided to be connected to the bottom passage 221, and the other end of the discharge passage 230, that is, one surface on which the outlet opening 231 is formed, may be provided to face one surface of the backflow prevention chamber. In addition, the discharge passage 230 to one end (upper portion) of the discharge passage 230 and the other end (lower portion) of the discharge passage 230 may be formed to be inclined at a predetermined angle with respect to the vertical.

As described above, the discharge passage 230, specifically, one surface 230a of the discharge passage 230 in which the outlet opening 231 is formed, may be provided to face each other with one surface 400a of the backflow prevention chamber part 400, and may be provided to face each other in the vertical direction.

In addition, the outlet opening 231 may be provided to protrude at least one or more from the one surface 230a of the discharge passage 230, and may be provided to be connected to the backflow prevention chamber part 400.

The discharge part 300 may be provided in the vertical direction from the inside of the housing 100 to the lower portion of the housing 100, and may be connected to the outlet 102 of the housing 100. The discharge part 300 may be provided to receive the medical fluid from the trap flow part 200 and discharge the medical fluid. The discharge part 300 may be provided in a cylindrical shape provided so as to increase in diameter from top to bottom.

Figure 4:
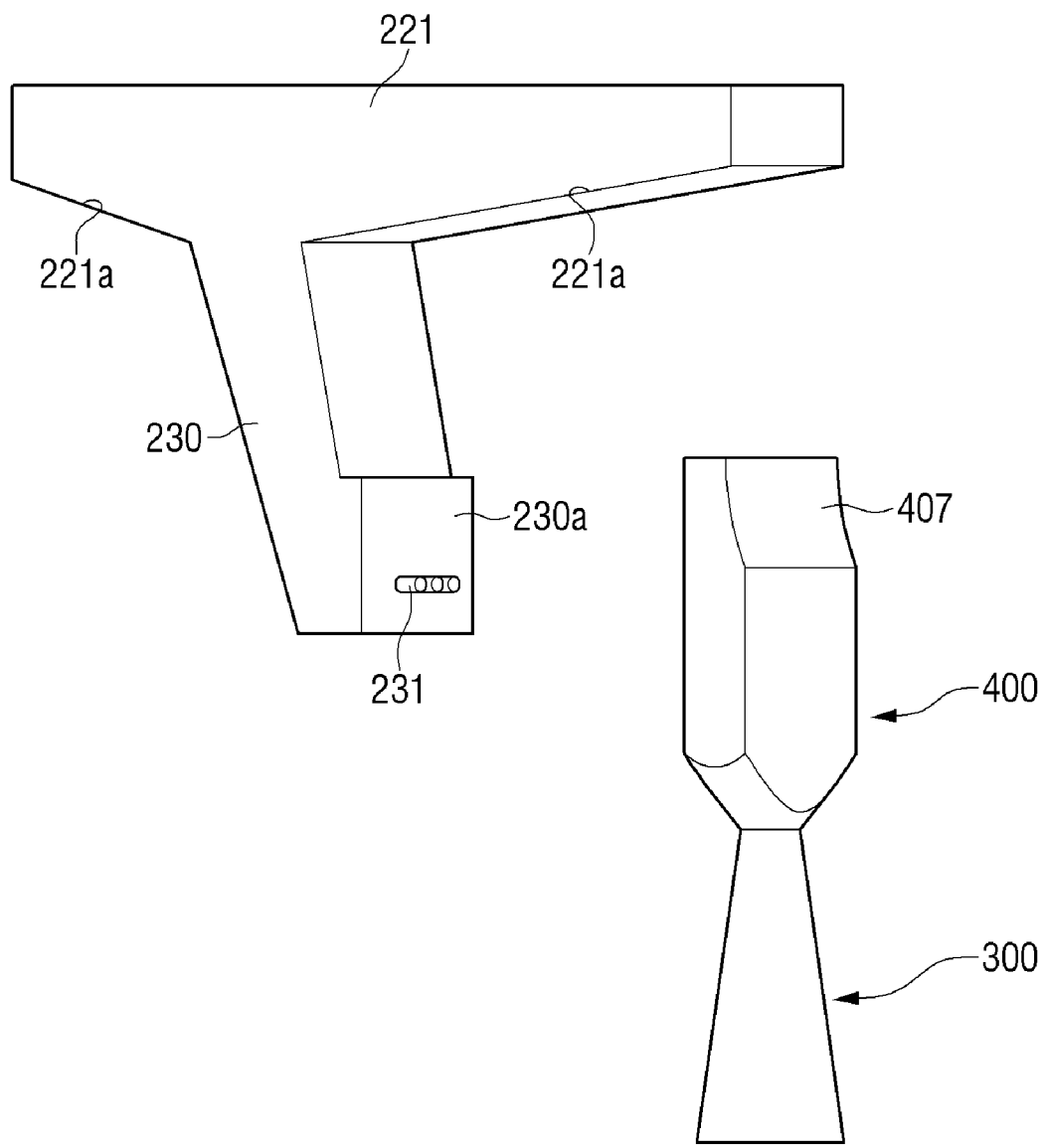
FIG. 4 is a perspective view in one direction in which the shortest part of a main flow passage and a discharge passage and a backflow prevention chamber part are separated in the apparatus for preventing the backflow according to the embodiment of the present invention.
Figure 5:
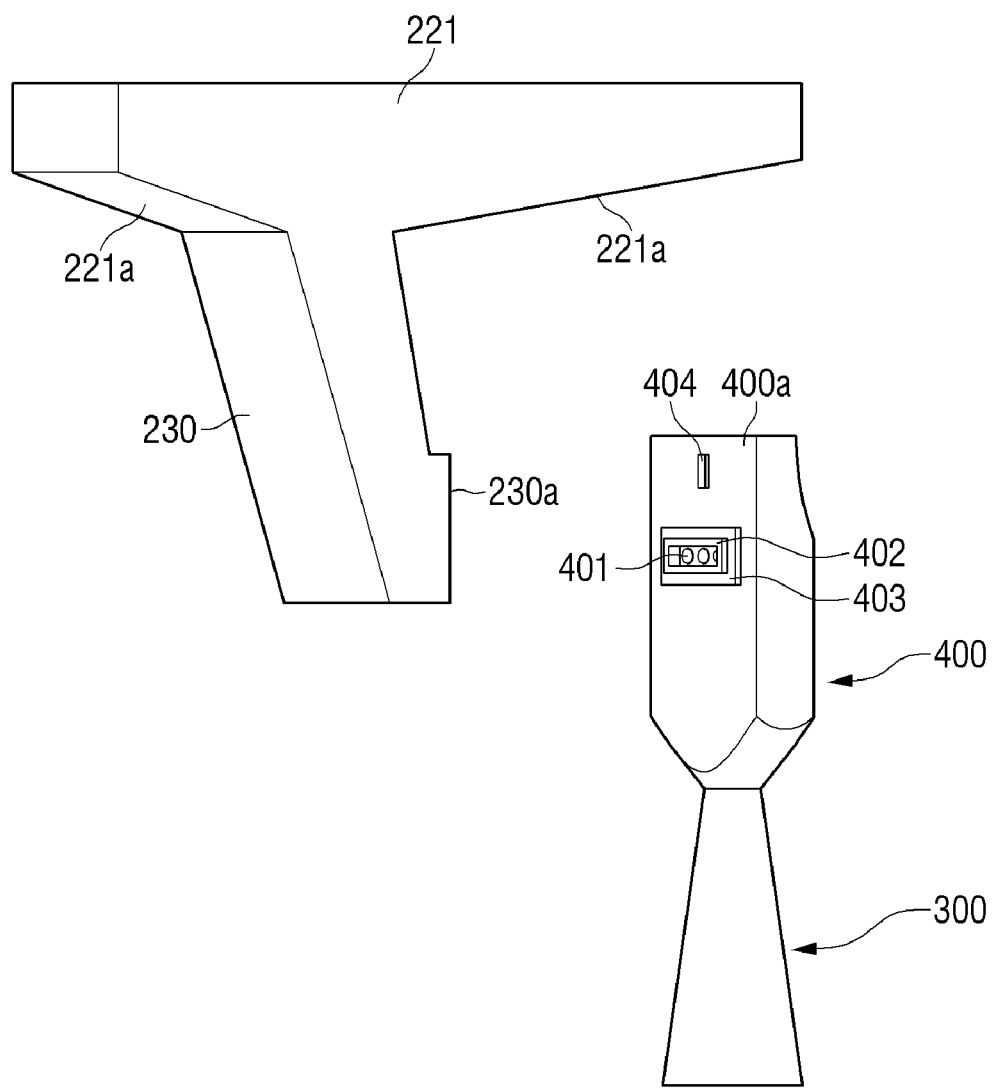
FIG. 5 is a perspective view in the other direction in which the shortest part of a main flow passage and a discharge passage and a backflow prevention chamber part are separated in the apparatus for preventing the backflow according to the embodiment of the present invention.
Figure 6:
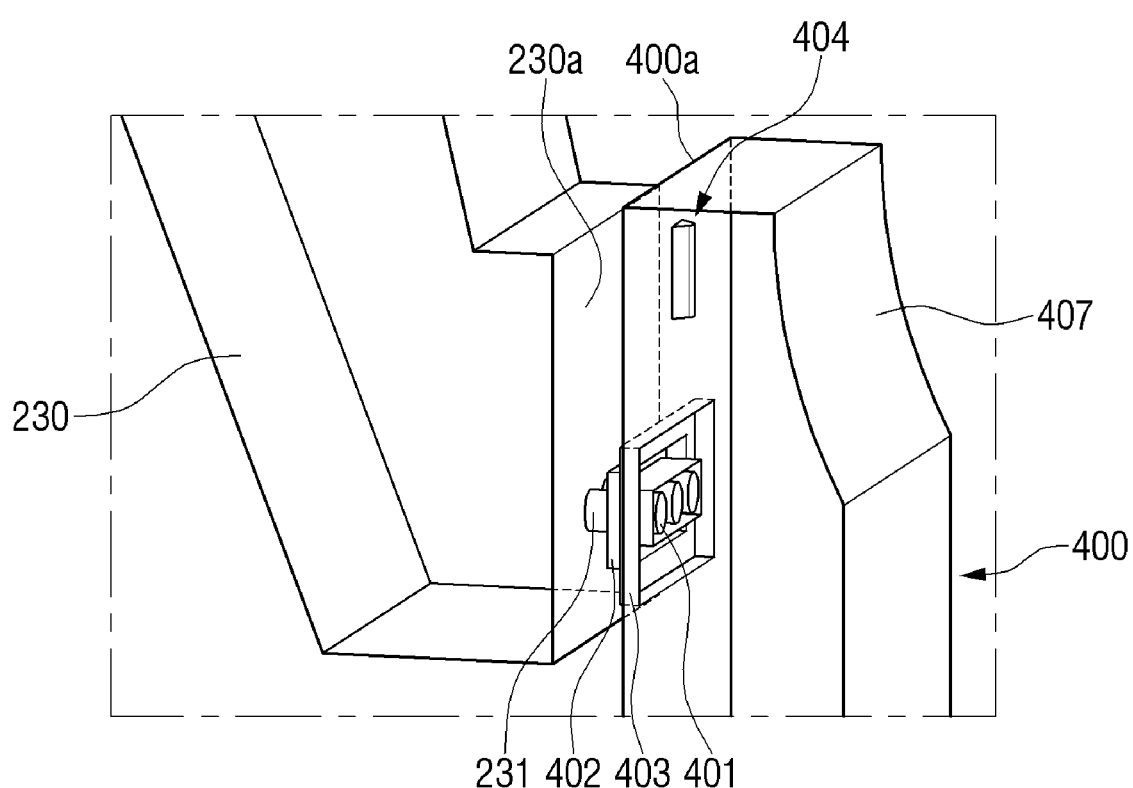
FIG. 6 is a perspective view schematically showing a coupled state of the discharge passage connected to the shortest main flow passage and the backflow prevention chamber part in the apparatus for preventing the backflow according to the embodiment of the present invention.
Figure 7:
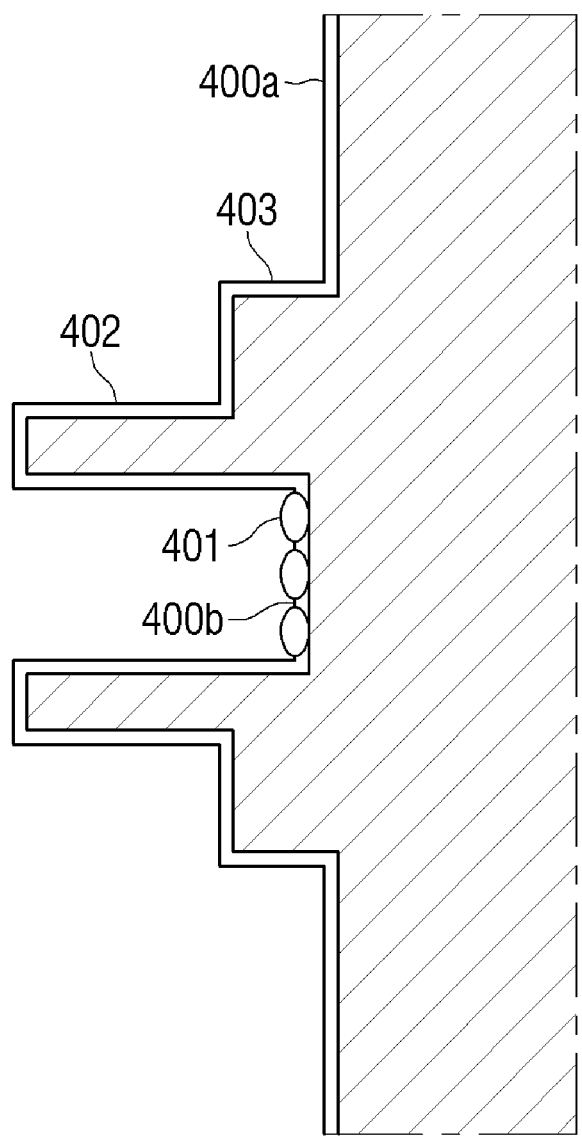
FIG. 7 is a side cross-sectional view schematically showing a shape around an inlet opening of the backflow prevention chamber part in the apparatus for preventing the backflow according to the embodiment of the present invention.

FIG. 4 is a perspective view in one direction in which the shortest part of the main flow passage 220 and the discharge passage 230 and the backflow prevention chamber part 400 are separated in the apparatus 10 for preventing the backflow according to the embodiment of the present invention. FIG. 5 is a perspective view in the other direction in which the shortest part of the main flow passage 220 and the discharge passage 230 and the backflow prevention chamber part 400 are separated in the apparatus 10 for preventing the backflow according to the embodiment of the present invention. FIG. 6 is a perspective view schematically showing a coupled state of the discharge passage 230 connected to the shortest main flow passage 220 and the backflow prevention chamber part 400 in the apparatus 10 for preventing the backflow according to the embodiment of the present invention. FIG. 7 is a side cross-sectional view schematically showing a shape around the inlet opening 401 of the backflow prevention chamber part in the 10 apparatus for preventing the backflow according to the embodiment of the present invention.

Referring to FIGS. 4 to 7, the backflow prevention chamber part 400 according to the embodiment of the present invention may be provided between the trap flow part 200 and the discharge part 300. The backflow prevention chamber part 400 may be provided to enable the flow of the medical fluid from the trap flow part 200 to the discharge part 300 and to block the flow of the medical fluid from the discharge part 300 to the trap flow part 200.

The inlet opening 401 may be formed on one surface of the backflow prevention chamber part 400, in which the inlet opening 401 is connected to the outlet opening 231 by introducing a plurality of the outlet openings 231 protruding from one surface of the discharge passage 230. The medical fluid introduced into the discharge passage 230 may be provided to be introduced into the inlet opening 401 through the outlet opening 231. In the embodiment of the present invention, it is described as an example in which the outlet opening 231 is formed in three cylindrical shapes protruding horizontally from one surface of the discharge passage 230. However, it is not limited thereto, and as long as the shape is such that it protrudes from one surface of the discharge passage 230 and the medical fluid is introduced into the backflow prevention chamber part 400, the shape may be changed or deformed. In addition, the inlet opening 401 may be formed as a circular opening so that the outlet opening 231 having a cylindrical shape may be introduced.

In addition, a groove may be formed inside one surface of the backflow prevention chamber part 400 while surrounding the inlet opening 401 around one surface of the backflow prevention chamber part 400 on which the inlet opening 401 is formed. Specifically, one surface 400a of the backflow prevention chamber part 400 and a formation surface 400b in which the inlet opening 401 is formed may form the same position. In addition, two stepped contact grooves may be formed. Specifically, an inner contact groove 402 protruding in the direction facing the trap flow part 200 between the one surface 400a of the backflow prevention chamber 400 and the formation surface 400b around the one surface 400a may be provided. In addition, an outer contact groove 403 protruding stepwise between the one surface of the backflow preventing chamber 400 and the inner contact groove 402 may be formed around the inner contact groove 402.

A stopper protrusion 404 protruding into the inside of the backflow prevention chamber part 400 may be formed on an upper side of the one surface of the inner side of the backflow prevention chamber part 400. The stopper protrusion 404 may be provided to limit movement of the backflow prevention member 500 in the left and right directions by engaging with a guide groove 525 of the backflow prevention member 500 to be described later.

Figure 8:
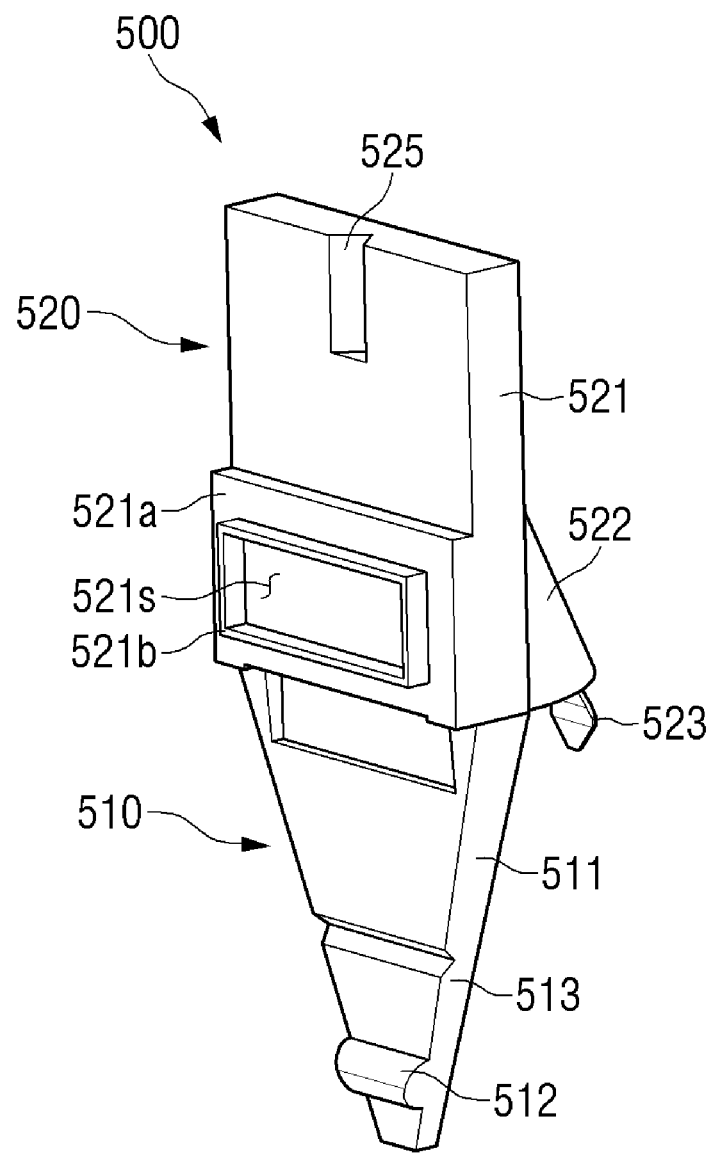
FIG. 8 is a schematic perspective view of a backflow prevention member in one direction in the apparatus for preventing the backflow according to the embodiment of the present invention.
Figure 9:
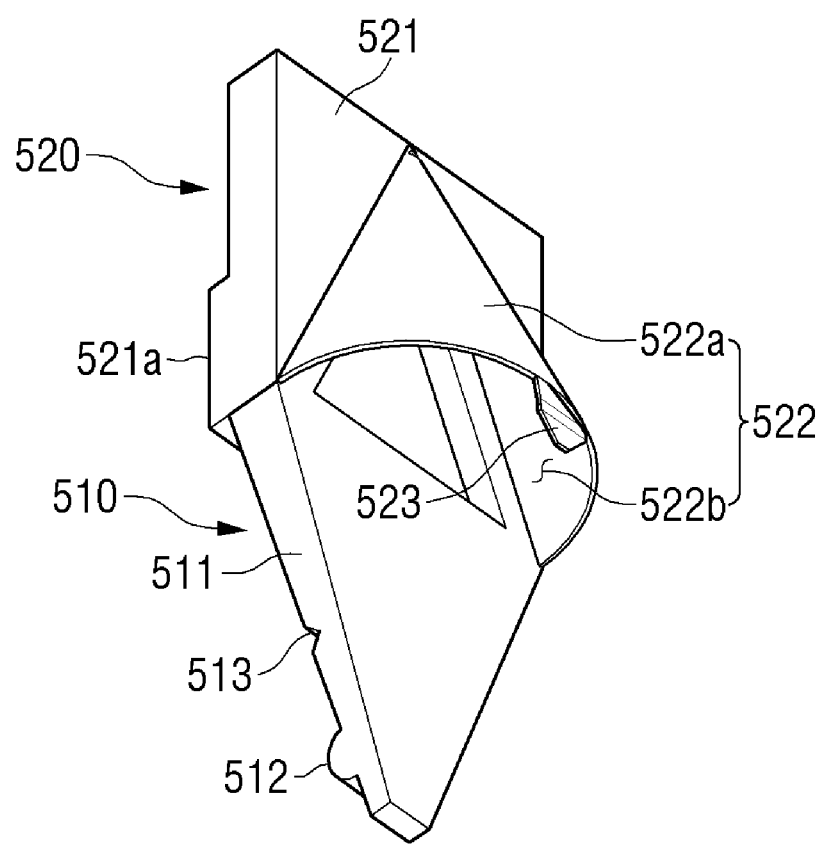
FIG. 9 is a schematic perspective view of the backflow prevention member in the other direction in the apparatus for preventing the backflow according to the embodiment of the present invention.
Figure 10:
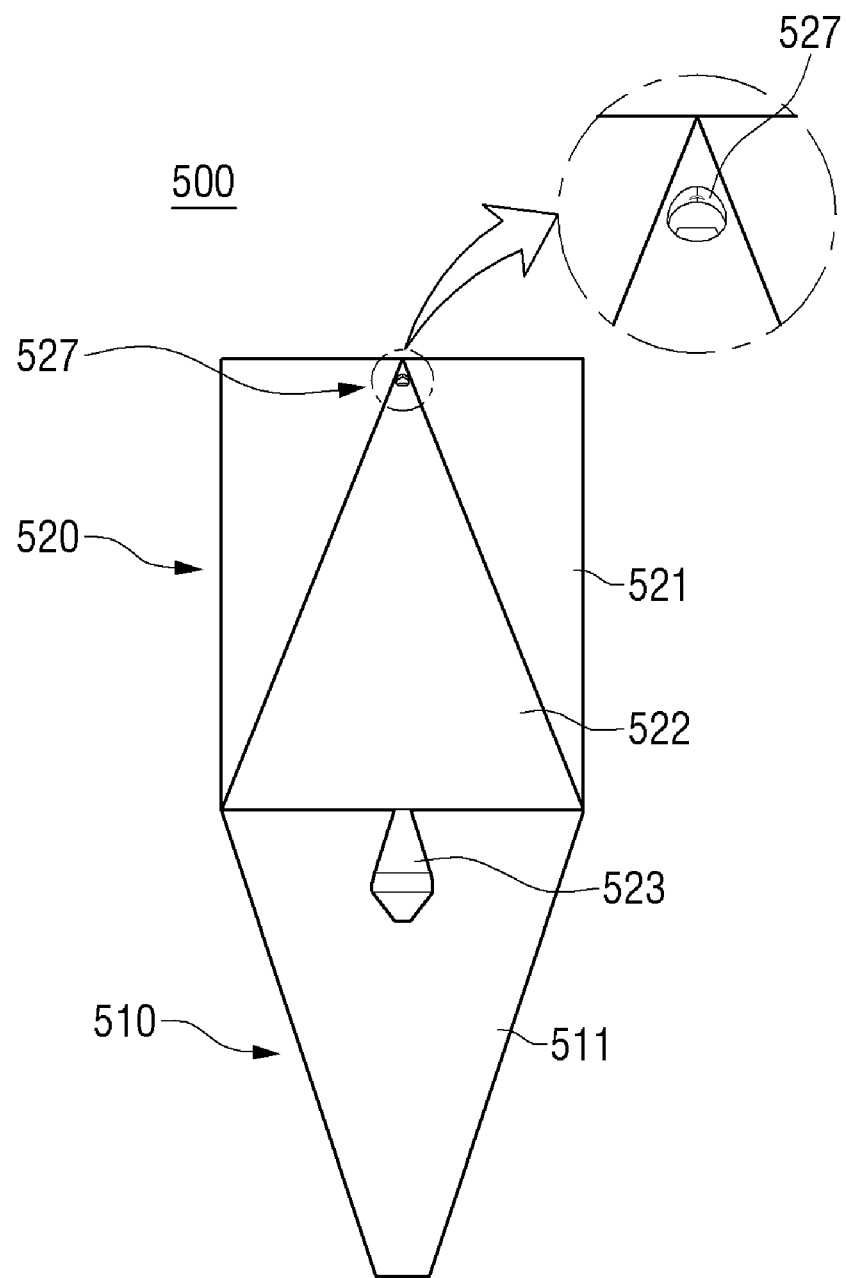
FIG. 10 is a rear plan view of the backflow prevention member in the apparatus for preventing the backflow according to the embodiment of the present invention.
Figure 11:
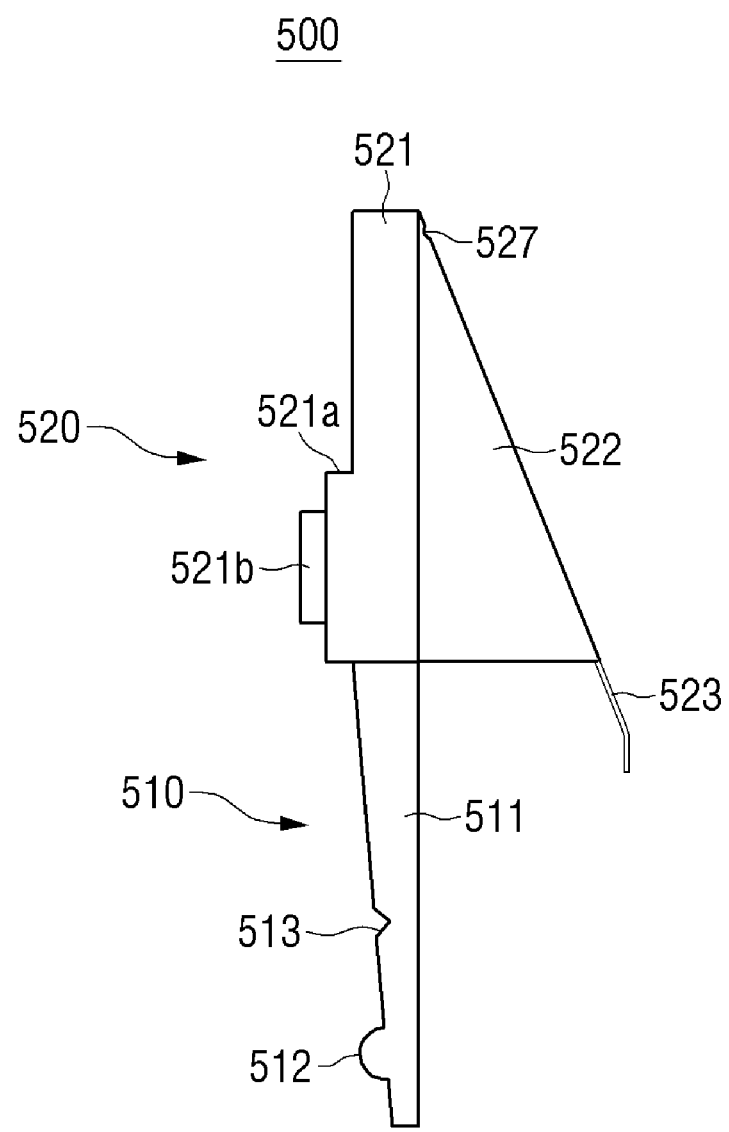
FIG. 11 is a side view of the backflow prevention member in the apparatus for preventing the backflow according to the embodiment of the present invention.

An upper portion of the other one surface of the inner side of the backflow prevention chamber 400 may be provided with a contact inclined surface 407 having an inclined shape as it moves further downward. The contact inclined surface 407 may be provided to limit the bending of the plate-shaped backflow prevention member 500 by contacting the plate-shaped backflow prevention member 500 when the medical fluid flows forward. FIG. 8 is a schematic perspective view of the backflow prevention member 500 in one direction in the apparatus 10 for preventing the backflow according to the embodiment of the present invention. FIG. 9 is a schematic perspective view of the backflow prevention member 500 in the other direction in the apparatus 10 for preventing the backflow according to the embodiment of the present invention. FIG. 10 is a rear plan view of the backflow prevention member 500 in the apparatus 10 for preventing the backflow according to the embodiment of the present invention. FIG. 11 is a side view of the backflow prevention member 500 in the apparatus 10 for preventing the backflow according to the embodiment of the present invention.

Referring to FIGS. 8 to 11, the backflow prevention member 500 may be provided in the backflow prevention chamber part 400 according to the embodiment of the present invention, in which the backflow prevention member 500 opens or closes the inlet opening 401 while allowing one-way movement of the medical fluid and blocking the reverse movement of the medical fluid or blood.

The backflow prevention member 500 according to the embodiment may be referred to as a plate-shaped backflow prevention member 500 in a plate shape, and hereinafter, may be referred to as a backflow prevention member 500. The backflow prevention member 500 may be provided on one surface of the inner side of the backflow preventing chamber 400 connected to the trap flow part 200. The backflow prevention member 500 may be in close contact with a periphery of the inlet opening 401 to which the outlet opening 231 is engaged, and may be provided to open or close the opening according to the forward flow and the backflow of the medical fluid.

The backflow prevention member 500 has a plate shape, and may be provided to be moved in a state in close contact with one side of the backflow prevention chamber part 400 in a direction away from a fixing part 512 (corresponding to a 'support 510' in the following description.) in the state in close contact.

Specifically, the backflow prevention member 500 may include a support 510 and a sealing 520.

The support 510 may be fixed to the one surface of the inner side of the backflow prevention chamber part 400 to fix the backflow prevention member 500 so as to be movable on the one surface of the inner side of the backflow prevention chamber part 400.

The support 510 may include a support plate 511, a fixing part 512 and a bending guide groove 513.

The support plate 511 is in close contact with the one surface of the inner side of the backflow prevention chamber 400 and the sealing 520 to be described later is connected to an upper side thereof, and may be formed in the form of an inverted triangle.

The fixing part 512 may be formed to protrude from an end of the support plate 511 in a corner portion of the inverted triangle shape. The fixing part 512 may be fixed to the one surface of the inner side of the backflow prevention chamber part 400. In the embodiment of the present invention, it may be described as an example in which the fixing part 512 is formed in a semi-cylindrical shape in the horizontal direction, so that the backflow prevention member 500 is rotatably coupled and fixed in the clockwise or counterclockwise direction (rotation between the inner surface and the other surface of the backflow prevention chamber 400). However, the fixing part 512 is not limited thereto, and as long as the backflow prevention member 500 is rotatably fixed from one surface to the other surface of the one surface of the inner side of the backflow prevention chamber part 400 or in the opposite direction, it may be modified or changed.

The bending guide groove 513 is provided on an upper portion of the fixing part 512 and is a retracted groove formed in a 'V' shape in the horizontal direction. The bending guide groove 513 may be formed to implement a predetermined bending of the support plate 511. In other words, when the backflow prevention chamber part 400 is bent in the direction of the other surface of the backflow prevention chamber part 400 around the fixing part 512, as the bending guide groove 513 is opened, bending may be fluidly possible.

Figure 12:
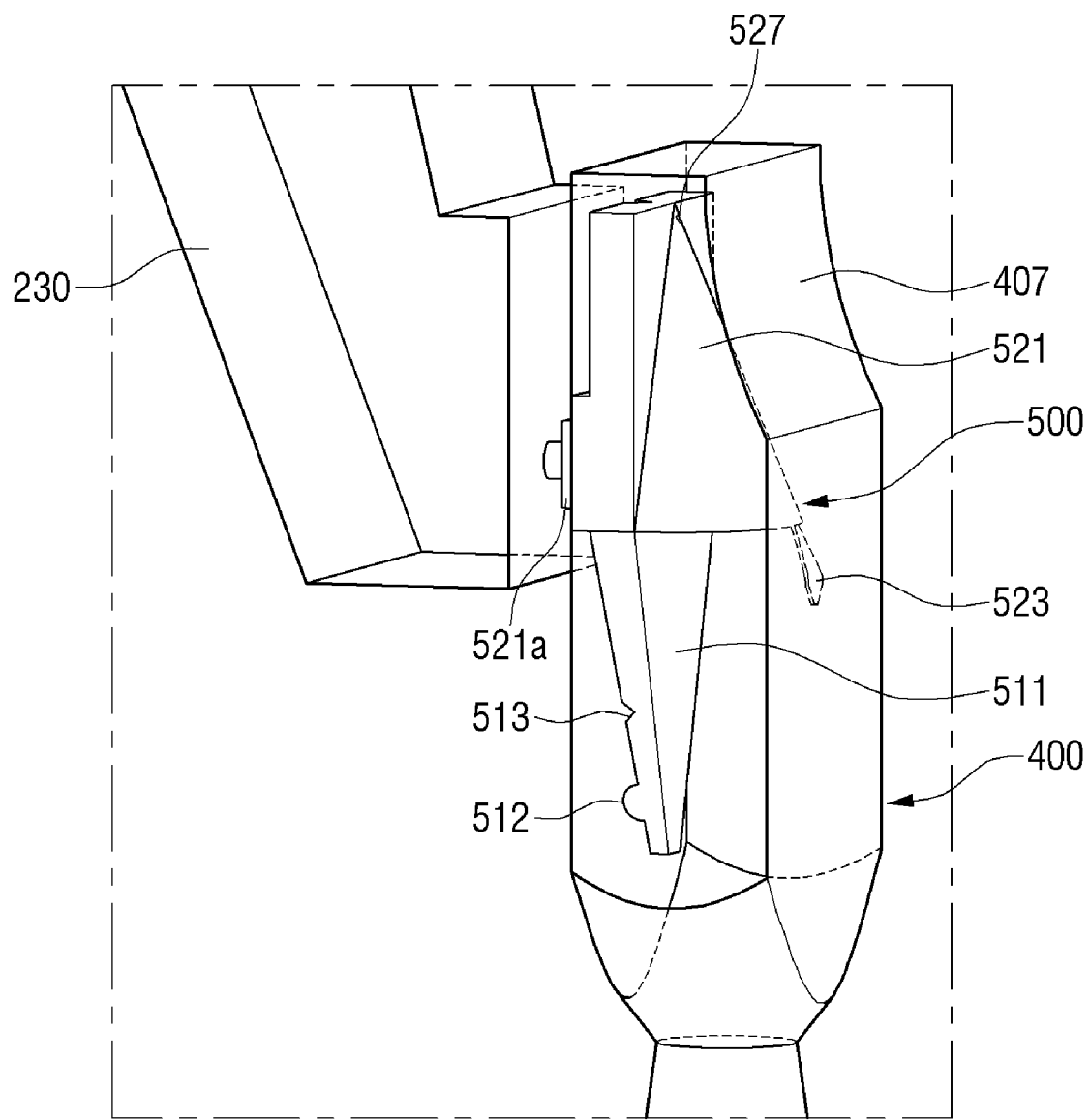
FIG. 12 is a perspective view illustrating a combination of the discharge passage, the backflow prevention chamber part, and the backflow prevention member in the apparatus for preventing the backflow according to the embodiment of the present invention.
Figure 13:
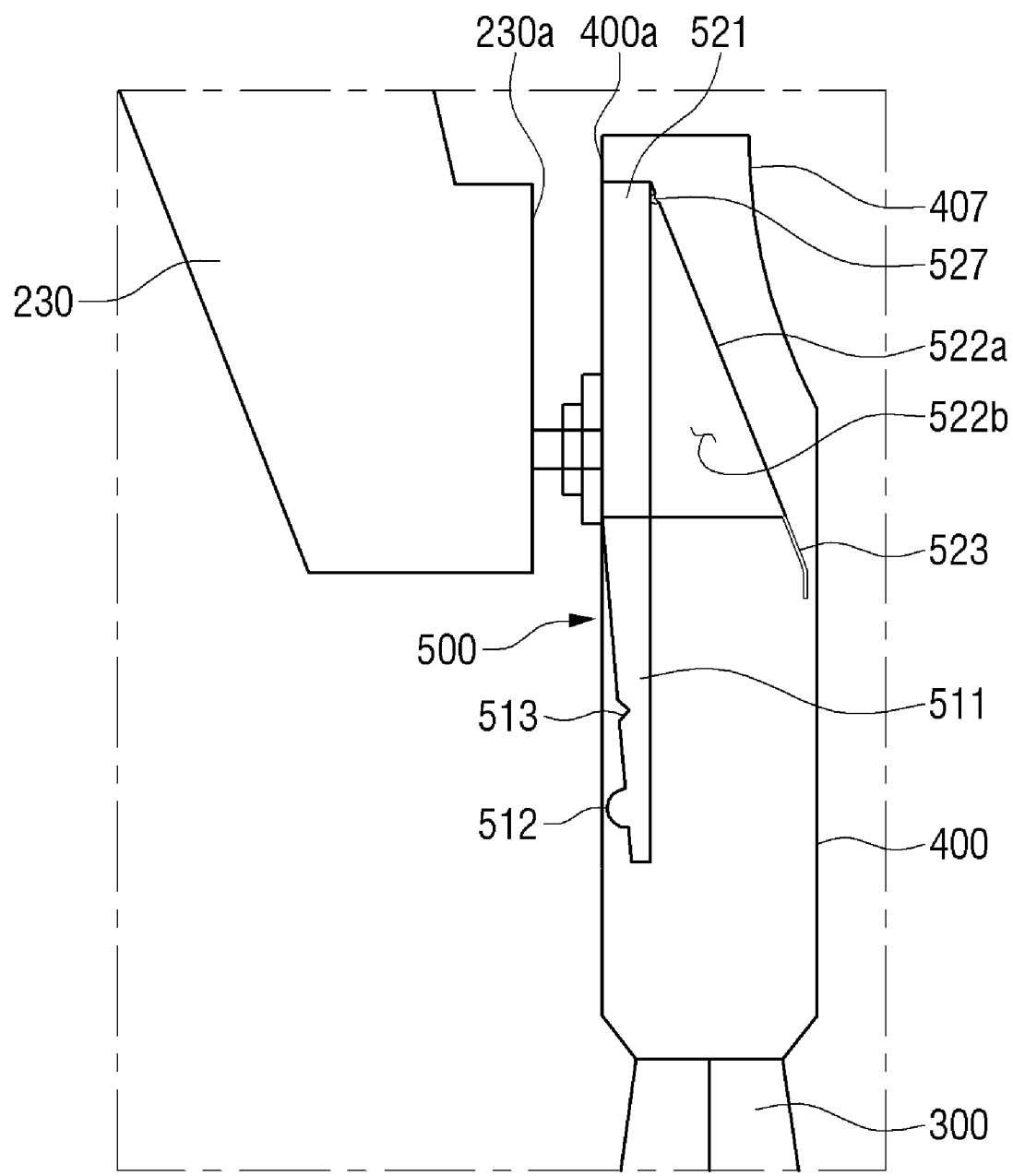
FIG. 13 is a side view illustrating the combination of the discharge passage, the backflow prevention chamber part, and the backflow prevention member in the apparatus for preventing the backflow according to the embodiment of the present invention.
Figure 14:
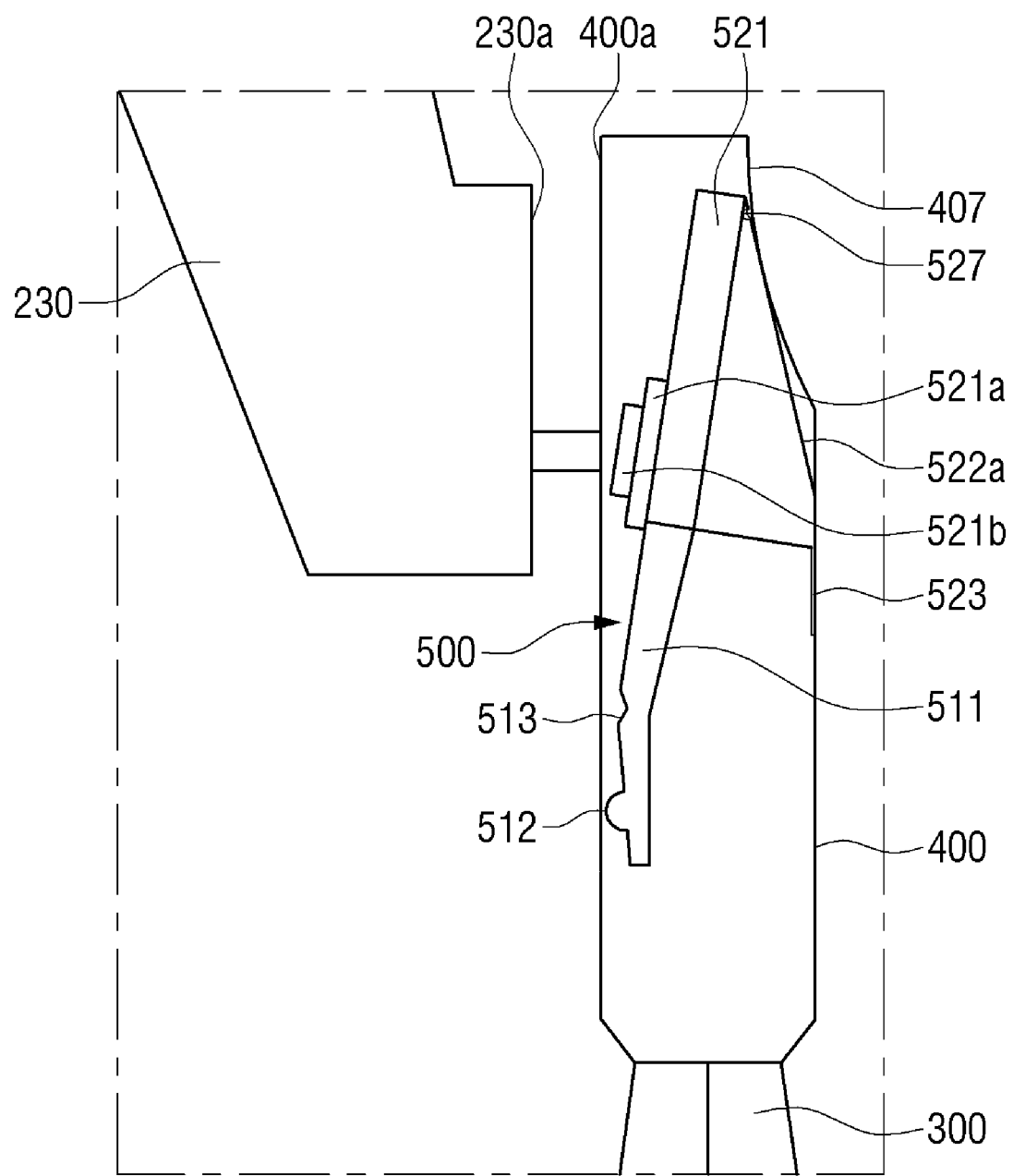
FIG. 14 is a view showing a state in which an outlet opening and an inlet opening are opened according to forward flow of a medical fluid in the apparatus for preventing the backflow according to the embodiment of the present invention.

FIG. 12 is a perspective view illustrating a combination of the discharge passage 230, the backflow prevention chamber part 400, and the backflow prevention member 500 in the apparatus 10 for preventing the backflow according to the embodiment of the present invention. FIG. 13 is a side view illustrating the combination of the discharge passage 230, the backflow prevention chamber part 400, and the backflow prevention member 500 in the apparatus 10 for preventing the backflow according to the embodiment of the present invention. FIG. 14 is a view showing a state in which the outlet opening 231 and the inlet opening 401 are opened according to the forward flow of the medical fluid in the apparatus 10 for preventing the backflow according to the embodiment of the present invention.

Referring to FIGS. 12 to 14 with FIGS. 8 to 11, the sealing 520 may be arranged above the support 510 and may have a shape extending from a top surface of the support 510. The sealing 520 may be provided to be bent between one surface and the other surface of the inner side of the backflow prevention chamber according to the moving direction of the medical fluid around the support 510. In addition, depending on the bending of the sealing 520, one surface of the sealing 520 may be implemented to open and close the inlet opening 401 while being in close contact or releasing the contact grooves 402 and 403, specifically, the inner contact groove 402 and the outer contact groove 403, and one surface of the inner side of the backflow prevention chamber part 400.

The sealing 520 according to the embodiment may include a sealing plate 521 and an opening and closing guide member 522.

The sealing plate 521 is a structure extending upward of the support 510. The sealing plate 521 may be provided to be bent between one surface and the other surface of the inner side of the backflow prevention chamber part 400 when the medical fluid flows forward or backward.

A protruding surface 521a that is engaged with the inner contact groove 402 and the outer contact groove 403 to seal them, and a contact protrusion 521b may be formed protruding on a front surface of the sealing plate 521.

The protruding surface 521a may be provided to protrude stepwise from the front surface of the sealing plate 521 and engage with the outer contact groove 403 to seal the inlet opening 401.

The contact protrusion 521b may be provided to protrude along an inner periphery of the protruding surface 521a and engage with the inner contact groove 402 to seal a periphery of the inlet opening 401. In addition, a space 521S in which a formation surface on which the inlet opening 401 is formed is accommodated may be formed inside the contact protrusion 521b.

Therefore, it may have a structure that when the backflow prevention member 500 comes into contact with one surface of the inner side of the backflow prevention chamber part 400, the contact protrusion 521b is seated in the inner contact groove 402 to be in close contact on one surface of the sealing plate 521, and the protruding surface 521a is engaged in close contact with the outer contact groove 403, thereby forming a double-sealing.

In addition, the guide groove 525 may be formed on an upper portion of a front surface of the sealing plate 521. When the sealing plate 521 is in close contact with the contact groove and a peripheral surface of the contact groove, the guide groove 525 may be seated on the stopper protrusion 404 described above to limit the flow of the sealing plate 521 to the left and right of the backflow prevention chamber 400.

The opening and closing guide member 522 may be provided on a rear surface of the sealing plate 521. The opening and closing guide member 522 is a structure provided to be in contact with the other surface of the inner side of the backflow prevention chamber part 400 or to receive pressure of a backward flowing medical fluid. Specifically, the sealing plate 521 is pushed to the other surface of the inner side of the backflow prevention chamber 400 according to the pressure of the medical fluid flowing forward when the sealing plate 521 is bent due to the forward flow of the medical fluid, and is bent. Here, as the bending of the backflow prevention member 500 occurs, the opening and closing guide member 522 may be in contact with the other surface of the inner side of the backflow prevention chamber part 400, and thus may be provided to limit the movement of the sealing plate 521. In addition, when the medical fluid is introduced into the opening and closing guide member 522 due to the backflow of the medical fluid, the sealing plate 521 is pushed to one surface of the inner side of the backflow prevention chamber 400 by the opening and closing guide member 522 provided with an inflow pressure of the fluid flowing back, and the sealing plate 521 may be pressed so as to be in close contact with one surface of the backflow prevention chamber part 400.

As described above, the opening and closing guide member 522 may be provided on the rear surface of the sealing plate 521. In addition, the opening and closing guide member 522 may be formed from an upper center to a lower end of the sealing plate 521, but may be provided to increase in width as it goes from the center of an upper end to the other end.

The opening and closing guide member 522 according to the embodiment of the present invention may form a guide body 522a formed in a semi-conical shape whose width increases and whose width increases from the upper end to the lower end of the sealing plate 521. An inner side of the guide body 522a may form a hollow 522b. If the medical fluid or blood flows back from the bottom to the top of the backflow prevention chamber 400, as the medical fluid or blood is introduced into the inner hollow 522b of the guide body 522a, a high pressing force may be instantaneously generated. Accordingly, the sealing plate 521 may be pressed in close contact with one surface of the inner side of the backflow prevention chamber part 400.

A circumference of the guide body 522a may be in contact with the other surface of the inner side of the backflow prevention chamber 400 by the bending movement of the sealing plate 521 to form a movement limiting surface that limits the movement of the sealing plate 521.

Also, as described above, the hollow may push up the guide body 522a due to the inflow pressure of the backflow direction of the medical fluid and press the sealing plate 521 around the support 510 to be in close contact with one surface of the inner side of the backflow prevention chamber part 400.

A protrusion part 523 extending along an inclined direction of the movement limiting surface may be further provided at the center of a lower end of the guide body 522a.

When the medical fluid flows forward, the backflow prevention member 500 is pushed by the pressure of the medical fluid and moves toward an inner wall of the backflow prevention chamber part 400. Here, when the backflow prevention member 500 moves to the backflow prevention chamber part 400, the protrusion part 523 may be in contact with an inner wall surface of the backflow prevention chamber part 400 so that a high pressure due to the instantaneous movement of the backflow prevention member 500 is elastically transmitted to absorb shock in advance. As a result, it is possible to limit the instantaneous contact of the guide body 522a with the backflow prevention chamber part 400.

In addition, a control hole 527 for controlling the pressure of the medical fluid or blood flowing back into the hollow may be further provided at an upper end of the guide body 522a according to the embodiment of the present invention.

As described above, when the medical fluid or blood flows back instantaneously, as the medical fluid or blood is introduced into the hollow of the guide body 522a, the guide body 522a is moved to one surface of the inner side of the backflow prevention chamber 400. Here, when the medical fluid or blood is introduced into the hollow, in addition to the discharge of gas such as air filled in the hollow, a part of the medical fluid or blood that is instantaneously introduced is discharged through the control hole 527, thereby facilitating the introduction of the medical fluid and blood. Accordingly, it is possible to facilitate close contact of the backflow prevention chamber part 400.

As described above, the apparatus 10 for preventing the backflow have a structure in which the trap flow part 200 through which the medical fluid flows is easily moved from top to bottom by forming a folded passage, but it is not easy to flow from bottom to top. In addition, it may have a structure in which the backflow prevention chamber 400 and the backflow prevention member 500 are provided between the trap flow part 200 and the discharge part 300 to enable the forward flow of the medical fluid, but the backflow of the medical fluid or blood may be effectively blocked.

Hereinafter, another embodiment of the backflow prevention member that is provided in the backflow prevention chamber and may prevent the backflow of the liquid medicine may be described with reference to FIGS. 15 to 25.

Figure 15:
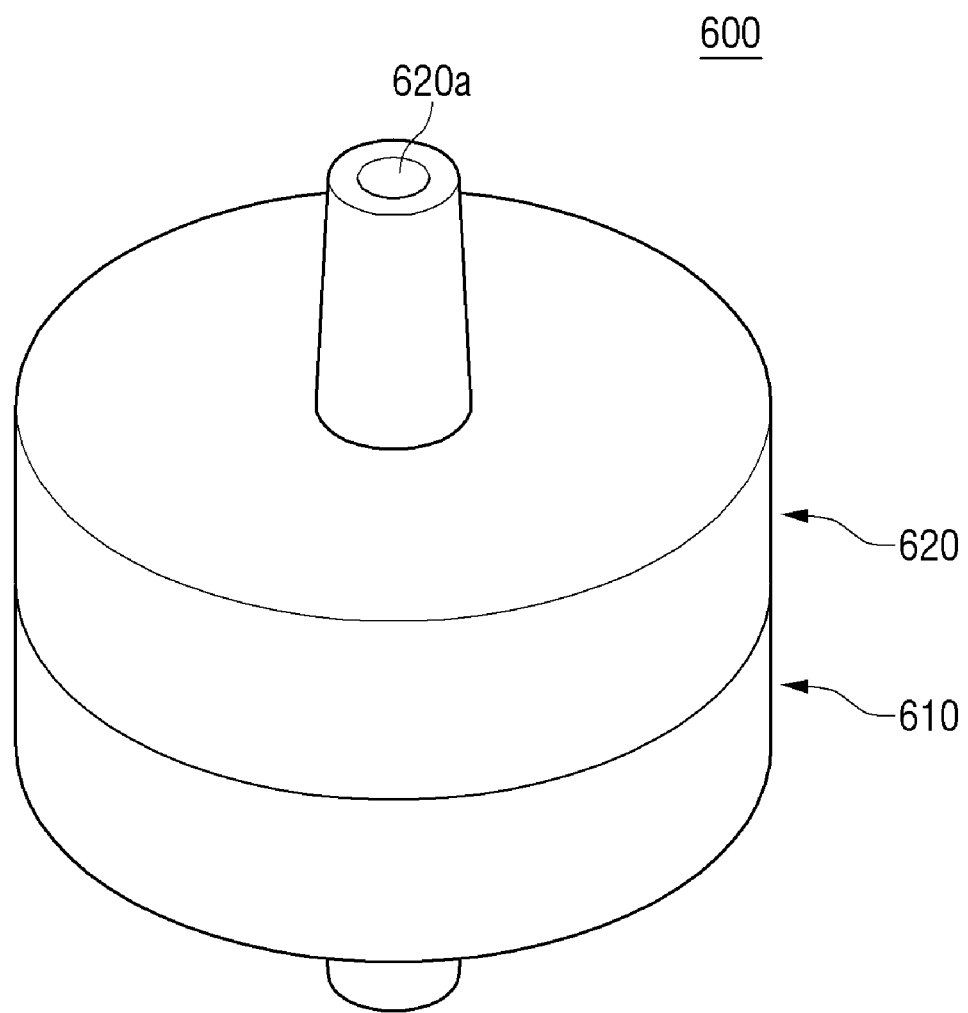
FIG. 15 is a combined perspective view showing the backflow prevention device according to an embodiment of the present invention.
Figure 16:
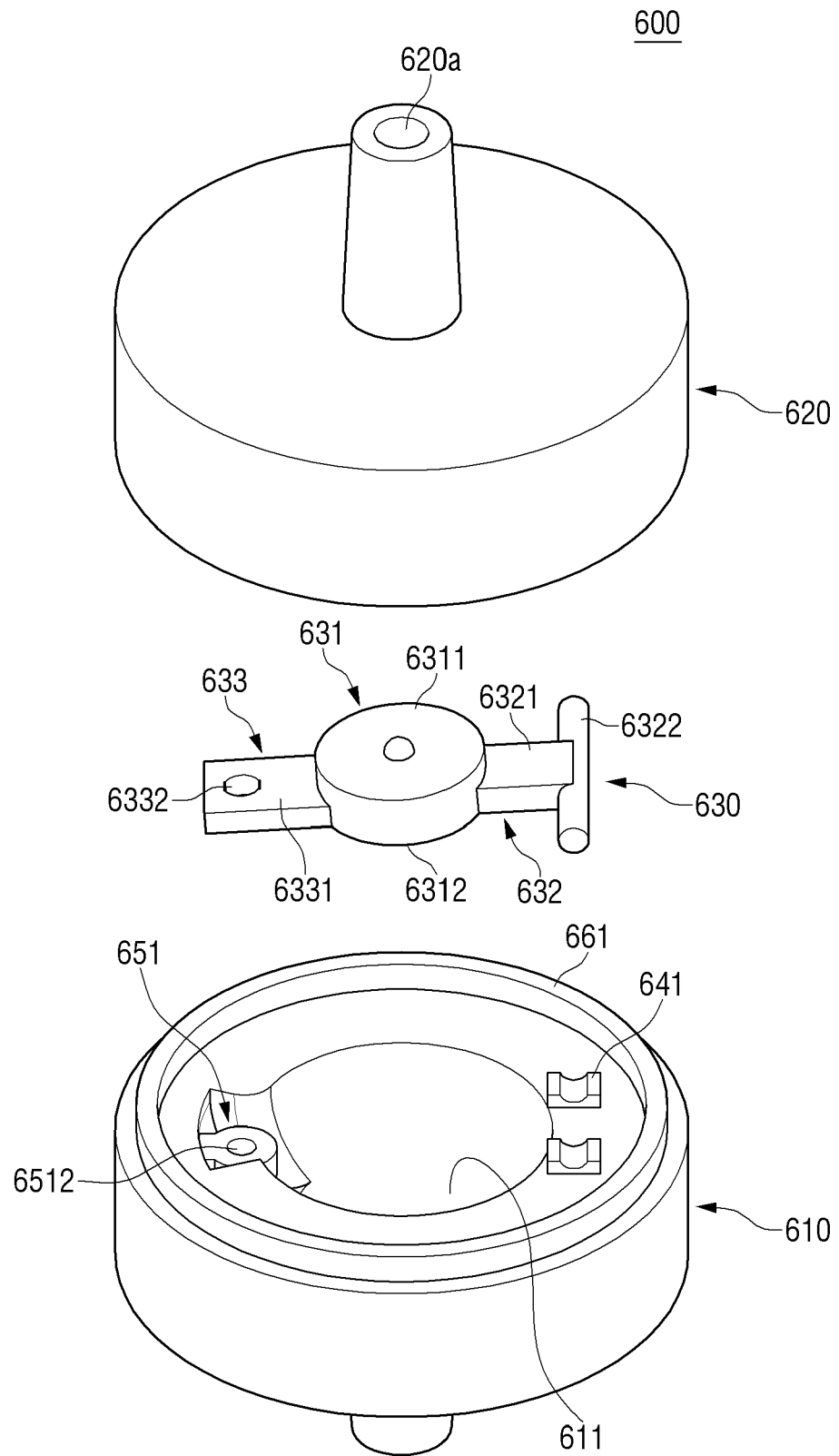
FIG. 16 is an exploded perspective view in one direction of the apparatus for preventing the backflow according to the embodiment of the present invention.
Figure 17:
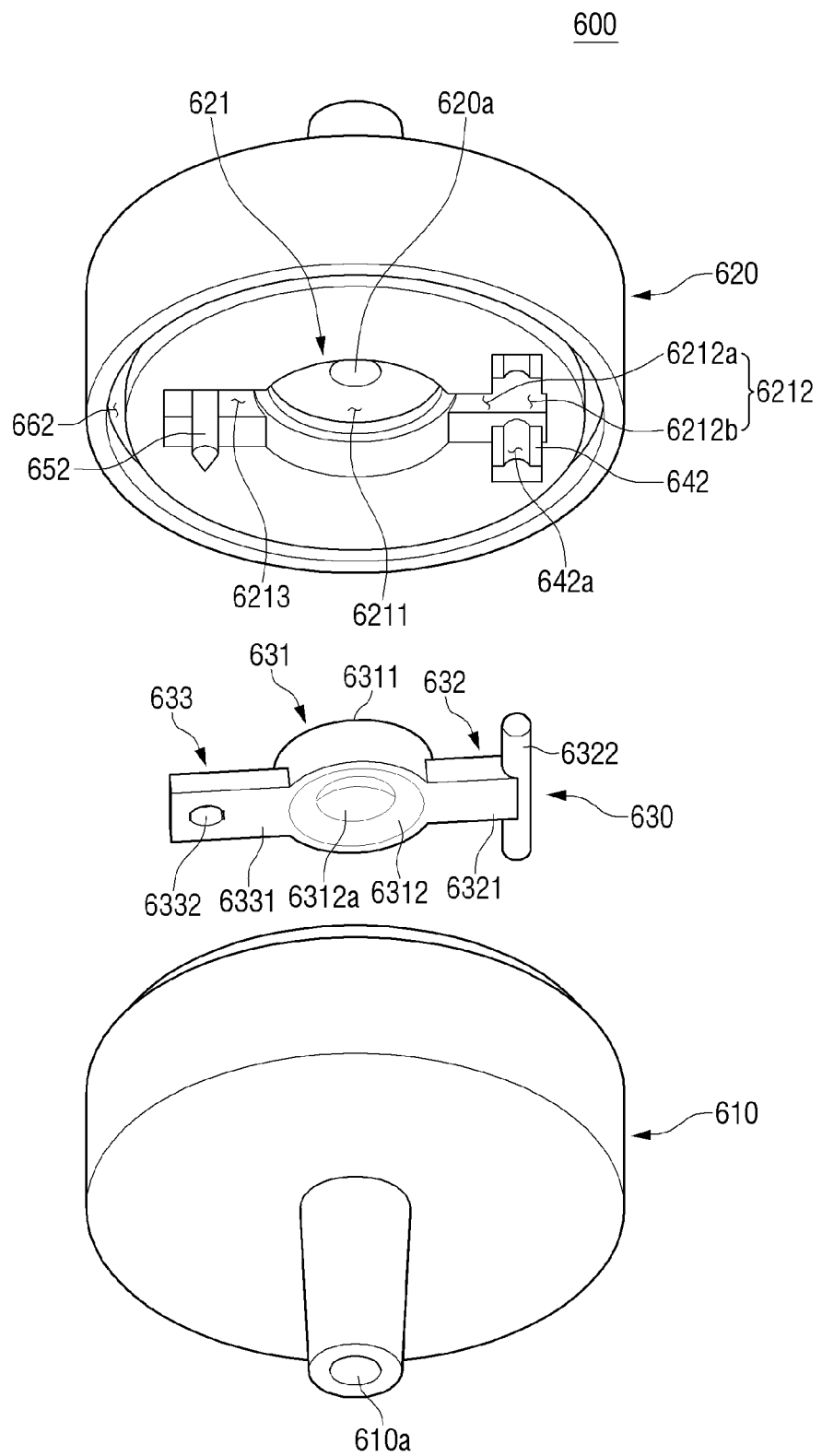
FIG. 17 is an exploded perspective view in the other direction of the apparatus for preventing the backflow according to the embodiment of the present invention.
Figure 18:
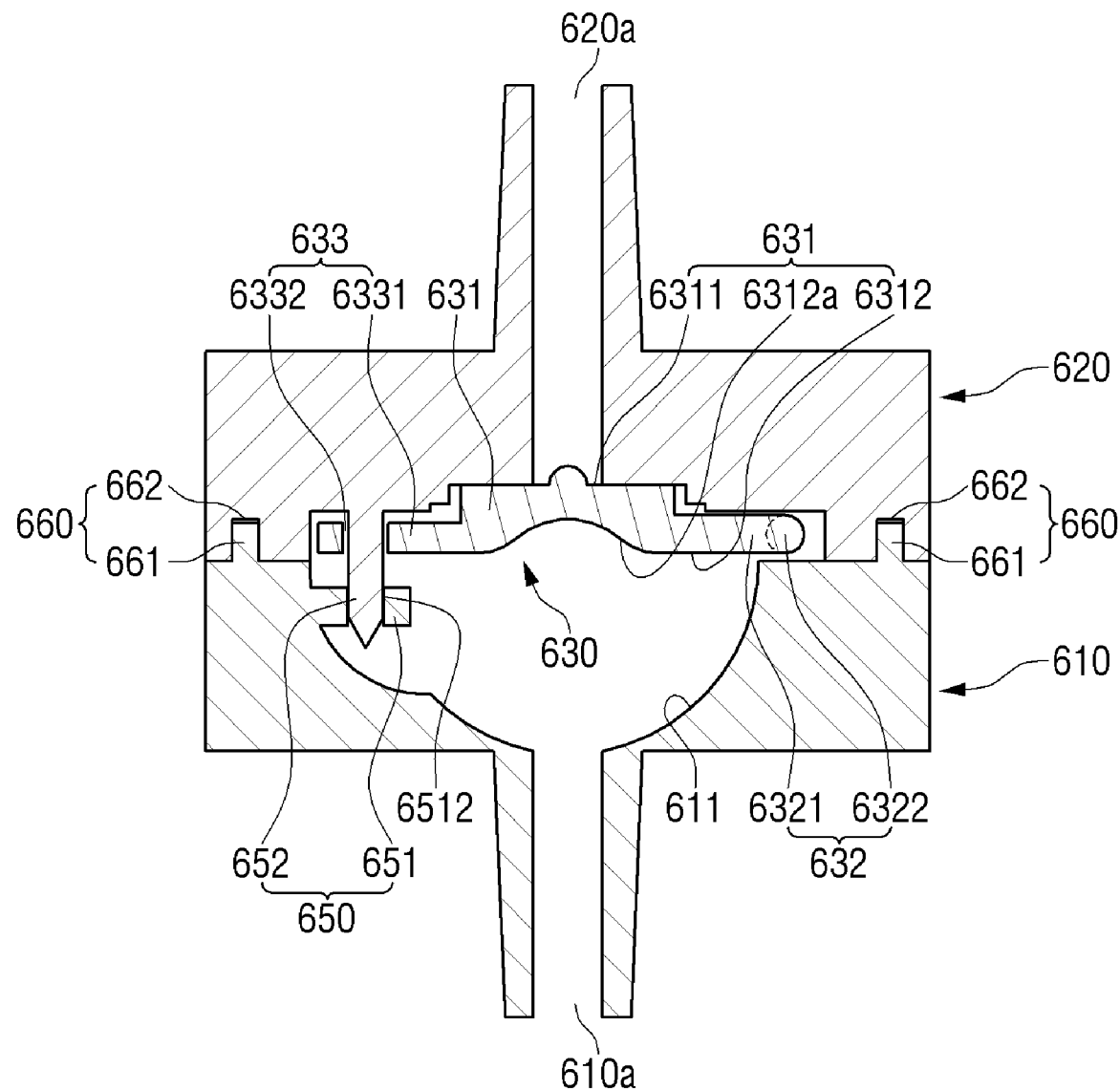
FIG. 18 is a combined cross-sectional view showing the backflow prevention device according to the embodiment of the present invention.

FIG. 15 is a combined perspective view showing an apparatus 600 for preventing backflow according to an embodiment of the present invention. FIG. 16 is an exploded perspective view in one direction of the apparatus 600 for preventing the backflow according to the embodiment of the present invention. FIG. 17 is an exploded perspective view in the other direction of the apparatus 600 for preventing the backflow according to the embodiment of the present invention. FIG. 18 is a combined cross-sectional view showing the apparatus 600 for preventing the backflow according to the embodiment of the present invention.

Referring to FIGS. 15 to 18, the apparatus 600 for preventing the backflow according to the embodiment of the present invention may include a first body 610, a second body 620, and a backflow prevention member 630. The backflow prevention member 630 according to the embodiment of the present invention may have a structure that when the first body 610 and the second body 620 are coupled while the backflow prevention member 630 is seated on the second body 620, the backflow prevention member 630 is closely coupled between the first body 610 and the second body 620. Accordingly, the apparatus 600 for preventing the backflow according to the embodiment of the present invention may be easily combined and disassembled, and a sealing force may be secured.

Specifically, the first body 610 may be configured in a cylindrical shape having a predetermined thickness. One surface of the first body 610 may be opened to form a hemispherical chamber 611 inside thereof. A discharge pipe connected to the chamber 611 to form a discharge passage 610a for discharging a medical fluid may be formed to protrude on the other surface of the first body 610. The configuration of the first body 610 may be described in detail with reference to FIGS. 17 and 18 to be described later.

The second body 620 may be seated and mounted on the opened one surface of the first body 610. A seating part 621 may be formed by inserted inward on one surface of the second body 620 (a surface facing one surface of the first body 610). In addition, an inlet pipe may be formed on the other surface of the second body 620 to form an inlet passage 620a connected to the seating part 621 to introduce a medical fluid. The configuration of the second body 620 may be described in detail with reference to FIGS. 23 and 24 to be described later.

The backflow prevention member 630 is configured between the first body 610 and the second body 620, and may be closely mounted in the seating groove 6211. The backflow prevention member 630 may have a plate-shaped spring structure in a disk shape. The backflow prevention member 630 may be configured to be rotated like a plate-shaped spring around one end of the backflow prevention member 630 according to forward flow of the medical fluid flowing in the inflow passage 620a and backflow generated in the discharge passage 610a, so as to open or close between the seating groove 6211 and the chamber 611. The backflow prevention member 630 may be described in detail with reference to FIGS. 15 and 16 to be described later.

Figure 19:
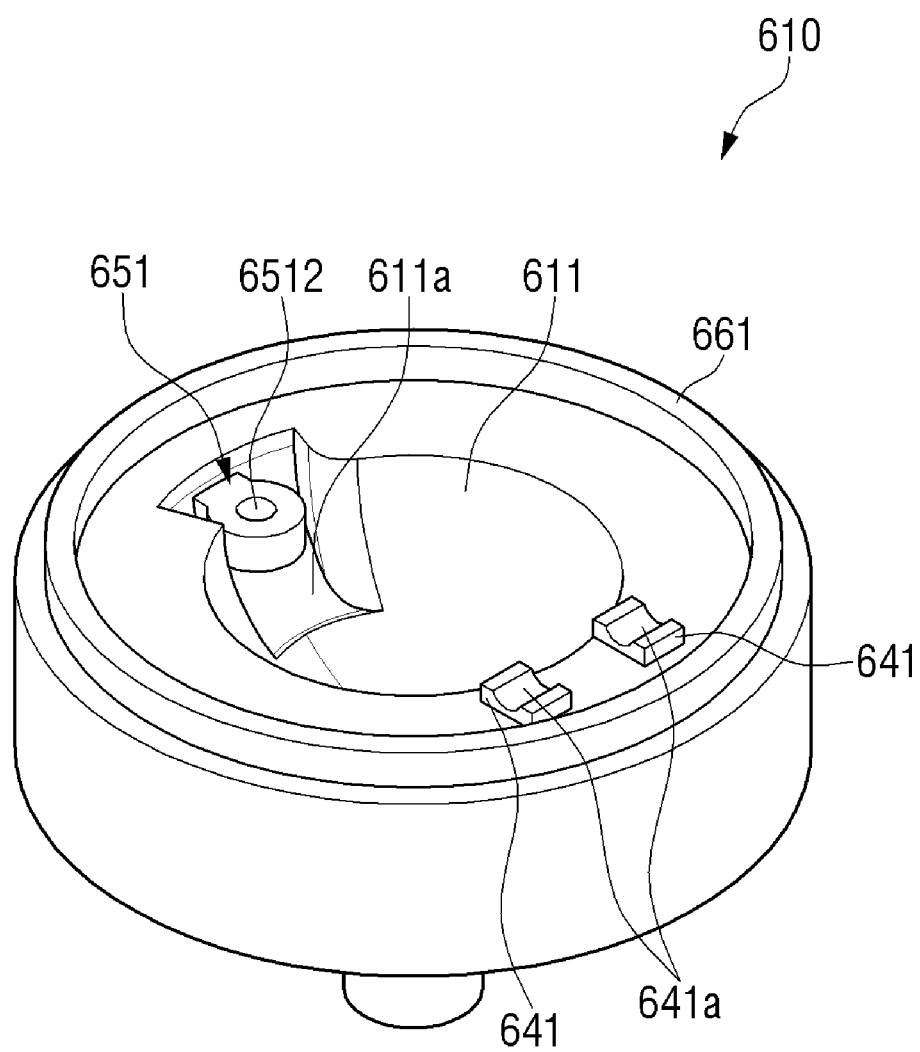
FIG. 19 is a perspective view of the backflow prevention member in the apparatus for preventing the backflow according to the embodiment of the present invention.

FIG. 19 is a perspective view of the backflow prevention member 630 in the apparatus 600 for preventing the backflow according to the embodiment of the present invention. FIG. 11 is a cross-sectional view of the backflow prevention member 630 in the apparatus 600 for preventing the backflow according to the embodiment of the present invention.

Figure 20:
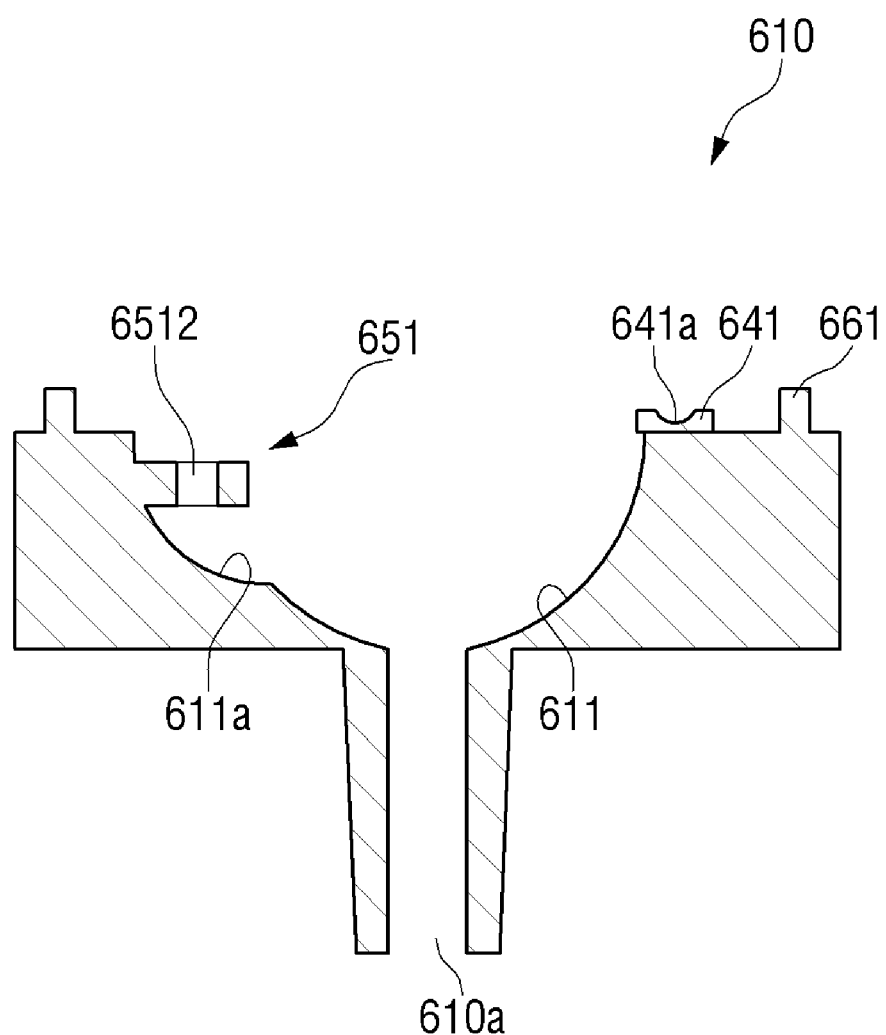
FIG. 20 is a cross-sectional view of the backflow prevention member in the apparatus for preventing the backflow according to the embodiment of the present invention.

Referring to FIGS. 19 and 20 (see also FIGS. 15 to 18), the backflow prevention member 630 according to the embodiment of the present invention may include a blocking body 631, a fixing protrusion part 632, and a moving protrusion part 633.

The blocking body 631 has a disk shape, and may be in close contact with the seating part 621 of the second body 620, specifically the seating groove 6211 to be described later. The blocking body 631 may implement driving such as a plate-shaped spring by the fixing protrusion part 632 and the moving protrusion part 633.

One surface of the blocking body 631 may include a contact surface 6311 that is in close contact with the seating groove 6211. In a state in which the blocking body 631 is in close contact with the seating groove 6211, the inflow passage 620a is in a closed state by the contact surface 6311 of the blocking body 631.

The other surface of the blocking body 631 may form a pressing surface 6312 in contact with the backward flowing medical fluid, and a pressing groove concavely drawn in a direction of the second body 620 may be formed on the pressing surface 6312. For example, when the medical fluid flows back, the medical fluid flowing back through the discharge passage 610a presses the concave pressing groove 6312a by a discharge pressure. Accordingly, the blocking body 631 may be in close contact with the seating groove 6211 and restrict the flow of the backward flowed medical fluid into the first body 610.

The fixing protrusion part 632 and the moving protrusion part 633 may protrude to one side and the other side of the blocking body 631, respectively. The fixing protrusion part 632 and the moving protrusion part 633 may be configured to be stepped downward from both ends of the blocking body 631. Accordingly, the fixing protrusion part 632 and the moving protrusion part 633 may have a thickness thinner than that of the blocking body 631. In addition, the backflow prevention member 630 may have a structure in which an end of the moving protrusion part 633 in a horizontal state is driven in a direction close to or away from the second body by rotating the fixing protrusion part 632, specifically, a rotation protrusion part 6322 to be described later about a central axis.

The fixing protrusion part 632 may protrude from one side of the blocking body 631 in a first direction, and may be rotatably seated and fixed between one surface of the first body 610 and one surface of the second body 620. Specifically, the fixing protrusion part 632 may be rotatably seated and fixed to the fixing part formed by a coupling of the first body 610 and the second body 620 to be described later. The fixing part may include a first fixing member 641 and a second fixing member 642.

The fixing protrusion part 632 may include a first protrusion part 6321 and the rotation protrusion part 6322.

The first protrusion part 6321 may protrude from the blocking body 631 in a first direction, and be mounted in the seating part 621, specifically a first extension groove 6212 to be described later, so that it is positioned between the first body 610 and the second body 620.

The rotation protrusion part 6322 may protrude in a vertical direction from an end of the first protrusion part 6321 so that the first protrusion part 6321 and the rotation protrusion part 6322 may be formed in a 'T' shape. The rotation protrusion part 6322 may be formed of a long cylindrical bar and may be rotatably fixed to the fixing part.

The moving protrusion part 633 may protrude from the other side of the blocking body 631 in a second direction opposite to the first direction. The moving protrusion part 633 may be provided between one surface of the first body 610 and one surface of the second body 620, and may be guided in an up-and-down direction between the chamber 611 and the seating part 621.

The moving protrusion part 633 may include a second protrusion part 6331 and a guide hole 6332.

The second protrusion 631 may protrude from the blocking body 631 in the second direction opposite to the first direction, and be seated on the seating part 621, specifically, the second extension groove 6213, so that it may be arranged between the first body 610 and the second body 620.

The guide hole 6332 may be formed at an end of the second protrusion 631, and the guide hole 6332 may be inserted into the moving guide 650 to be described later, specifically a guide protrusion 652. The guide hole 6332 may guide the up-and-down movement of the second protrusion part 6331 along the guide protrusion 652.

Figure 21:
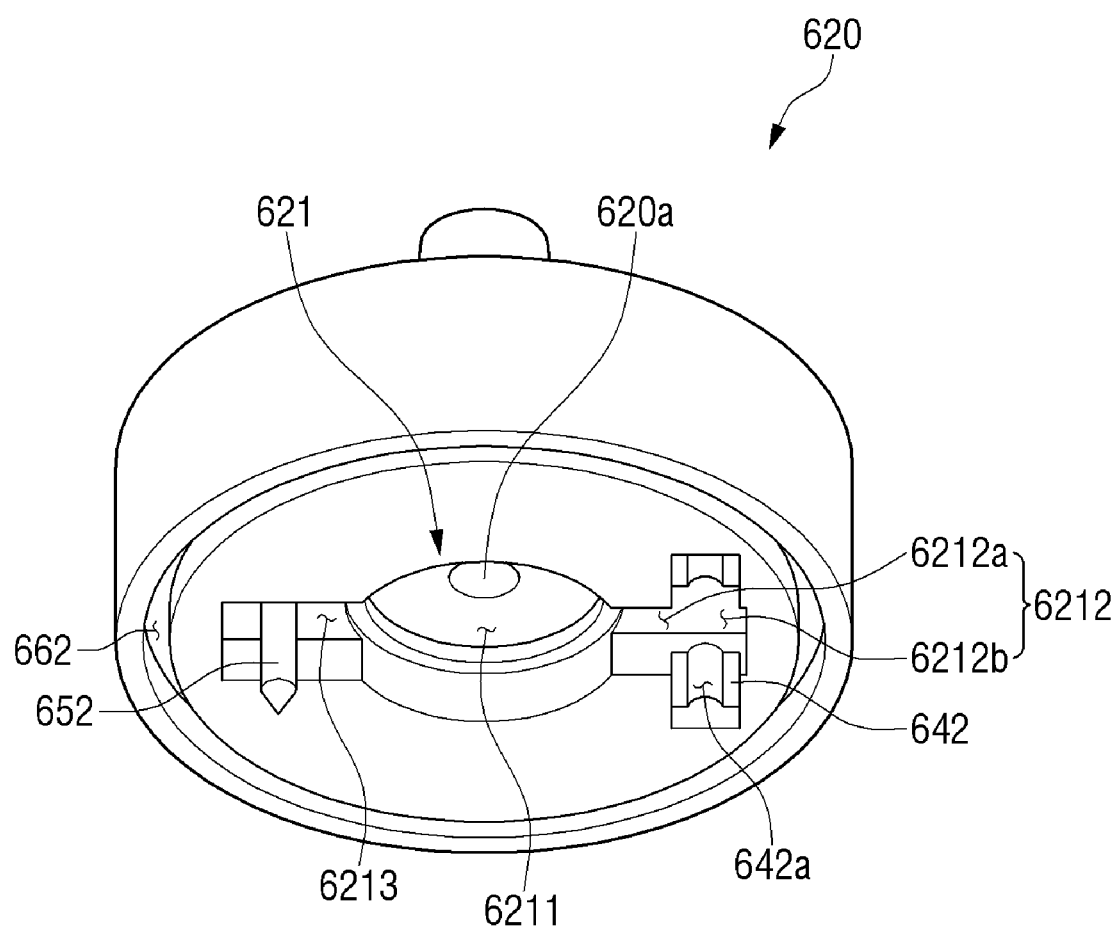
FIG. 21 is a perspective view of a first body in the apparatus for preventing the backflow according to the embodiment of the present invention.
Figure 22:
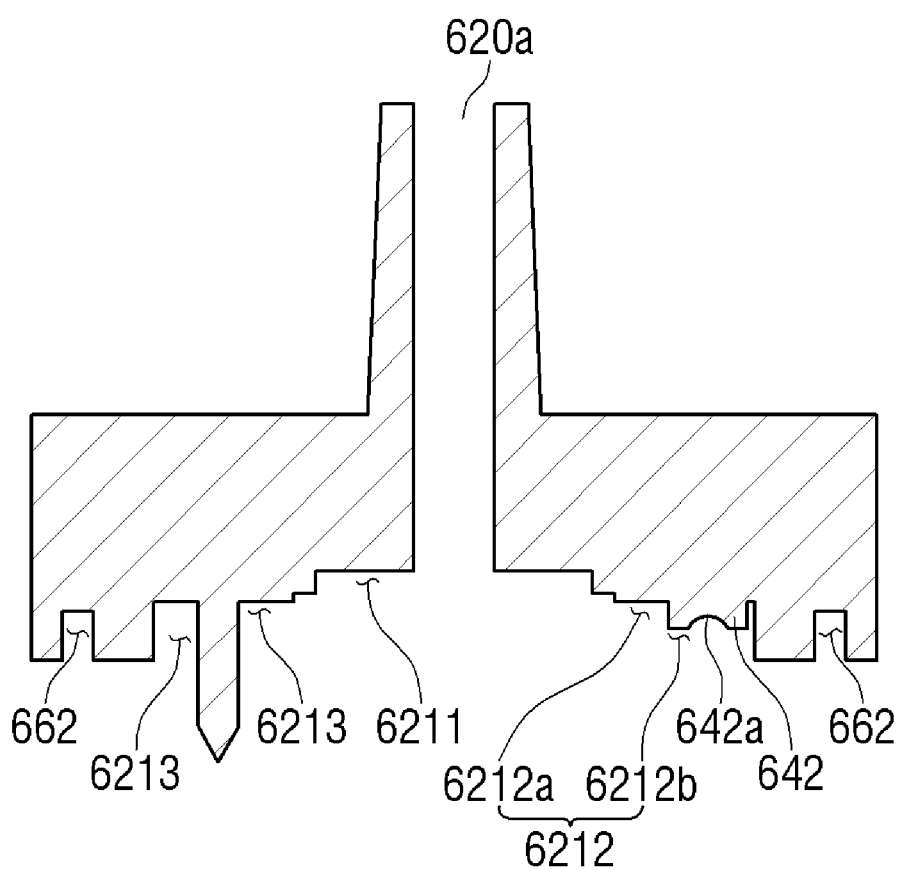
FIG. 22 is a cross-sectional view of the first body in the apparatus for preventing the backflow according to the embodiment of the present invention.
Figure 23:
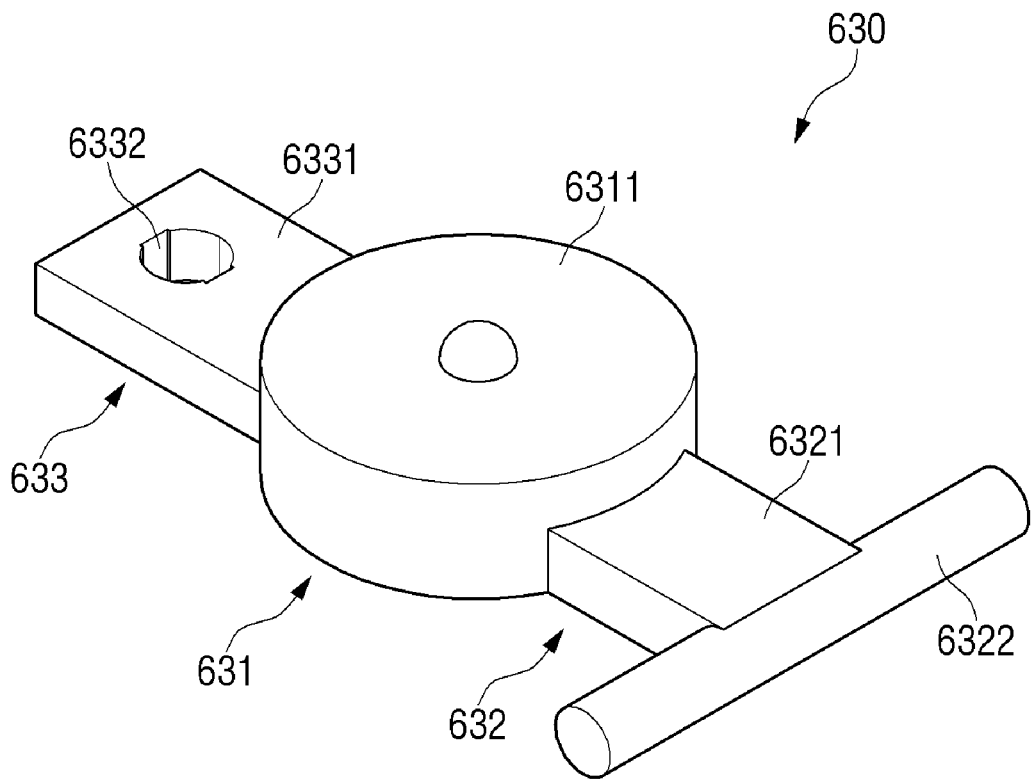
FIG. 23 is a perspective view of a second body in the apparatus for preventing the backflow according to the embodiment of the present invention.
Figure 24:
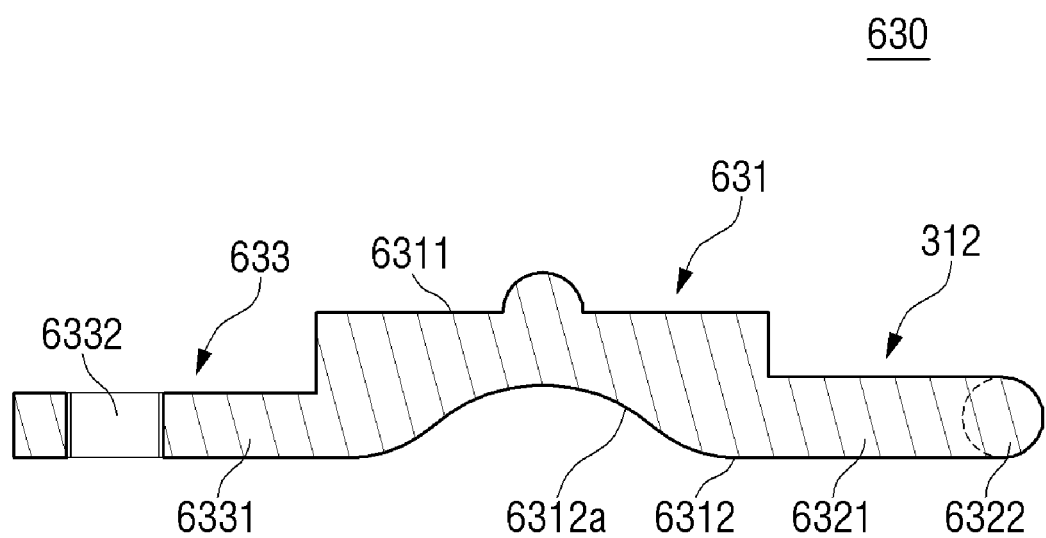
FIG. 24 is a cross-sectional view of the second body in the apparatus for preventing the backflow according to the embodiment of the present invention.

FIG. 21 is a perspective view of the first body 610 in the apparatus 600 for preventing the backflow according to the embodiment of the present invention. FIG. 22 is a cross-sectional view of the first body 610 in the apparatus 600 for preventing the backflow according to the embodiment of the present invention. FIG. 23 is a perspective view of the second body 620 in the apparatus 600 for preventing the backflow according to the embodiment of the present invention. FIG. 24 is a cross-sectional view of the second body 620 in the apparatus 600 for preventing the backflow according to the embodiment of the present invention.

Referring to FIGS. 21 to 24 (see also FIGS. 1 to 4), the first body 610 according to the embodiment of the present invention may be provided with the hemispherical chamber 611 inserted into an inner side, and the discharge passage 610a may be connected to an outer center of the chamber 611. A shape of the chamber 611 has been described as an example of a hemispherical shape, but is not limited thereto. For example, the shape of the chamber 611 and the discharge passage 610a may be formed in a funnel shape, so that when the backflow prevention member 630 is opened, the medical fluid being introduced from the inflow passage 620a is accommodated in the chamber 611 and may be discharged through the discharge passage 610a. As such, the shape of the chamber 611 and the discharge passage 610a may be variously modified or changed.

The seating part 621 may be provided on one surface (lower surface) of the second body 620 to be inserted into the inner side to seat the backflow prevention member 630.

The seating part 621 may include the seating groove 6211, the first extension groove 6212, and the second extension groove 6213.

The seating groove 6211 may be formed in a circular groove shape in the center of the second body 620, and the blocking body 631 may be seated and in close contact thereto. The inflow passage 620a may be connected to the center of the seating groove 6211. When the moving protrusion part 633 is moved up and down with the fixing protrusion part 632 as a central axis, as the blocking body 631 is in close contact with the seating groove 6211 and then the close contact state is released, the inflow passage 620a may be opened and closed. The seating groove 6211 may have a diameter smaller than an upper portion of the chamber 611. Accordingly, when the blocking body 631 in close contact with the seating groove 6211 is opened, the medical fluid may be introduced into the chamber 611 along the outside of the seating groove 6211.

The first extension groove 6212 may extend in the first direction from one end of the seating groove 6211 to an outer circumference of the second body 620, and the fixing protrusion part 632 may be seated therein. The first extension groove 6212 may extend stepped toward the first body 610 from an end of the seating groove 6211.

The first extension groove 6212 may be formed in a 'T' shape so that the fixing protrusion part 632 having a 'T' shape described above may be seated.

Specifically, the first extension groove 6212 may include a first protrusion part 6321 extension groove 6212*a* and a rotation protrusion extension groove 6212*b*.

The extension groove 6212*a* of the first protrusion part 6321 may extend in the first direction from the seating groove 6211, and the first protrusion part 6321 may be seated and in close contact thereto. The extension groove 6212*b* of the rotation protrusion may be formed to extend in a direction perpendicular to the extension groove of the second protrusion part 6331, and the rotation protrusion part 6322 may be seated and rotatably fixed thereto. The fixing part to be described later, specifically a second fixing member 642 may be formed in the extension groove of the rotation protrusion part 6322.

The second extension groove may extend in the second direction from the other side of the seating groove 6211 to the outer circumference of the second body 620, and the moving protrusion part 633 may be seated therein. The second extension groove 6213 may extend stepped toward the first body 610 from an end of the seating groove 6211.

Accordingly, an insertion thickness of the seating groove 6211 may be thicker than that of the first extension groove 6212 and the second extension groove 6213.

When the second body 620 is coupled onto the first body 610, a coupling part 660 may be formed to closely couple the first body 610 and the second body 620.

The coupling part 660 may be provided around one surface of the first body 610 and around one surface of the second body 620 that faces the first body 610, so that the first body 610 and the second body 620 may be closely coupled.

The coupling part 660 may include a coupling protrusion 661 and a coupling hole.

The coupling protrusion 661 may protrude in a closed loop shape along a circumference of one surface of the first body 610.

The coupling groove 662 may be formed to be inserted in a closed loop shape along a circumference of one surface of the second body 620 that faces one surface of the first body 610. The coupling groove 662 may correspond to the coupling protrusion 661 so that the coupling protrusion 661 may be inserted to be in close contact.

The fixing part and the moving guide 650 may be formed between the first body 610 and the second body 620 so that as the first body 610 and the second body 620 are coupled, the backflow prevention member 630 may be coupled and driven in the form of a plate spring.

The fixing part may be formed between the first body 610 and the second body 620 to the inside of the coupling part 660, and may be formed to rotatably fix the fixing protrusion part 632.

The fixing part may include a first fixing member 641 and a second fixing member 642.

The first fixing member 641 may be positioned on one surface of the first body 610 around the chamber 611, and may form a first groove 641*a* to be elongated in a semi-hollow shape.

In an embodiment of the present invention, it may be described as an example in which the first fixing members 641 are arranged to face each other and are provided to clamp both ends of the fixing guide as they are coupled with the second fixing members 642 to be described later. However, the first fixing member 641 may be variously modified or changed such that it may be formed to be elongated in the longitudinal direction.

The second fixing member 642 may be positioned in the extension groove 6212*b* of the rotation protrusion, and may form a semi-hollow-shaped second groove 642*a* corresponding to the semi-hollow-shaped groove of the first fixing member 641. It may be described as an example in which the second fixing members 642 are arranged opposite to each other at both ends of the extension groove 6212*b* of the rotation protrusion, and clamp both ends of the fixing guide as they engage with the first fixing member 641.

However, as described above, the second fixing member may also be formed to be elongated in the longitudinal direction in the extension groove 6212*b* of the rotation protrusion. Unlike this, the second fixing member may be provided to be positioned at the center of the first fixing member 641 facing each other, and to be formed to clamp the fixing guide. As such, the second fixing member may be modified in various ways.

When the first body 610 and the second body 620 are coupled, the fixing protrusion part 632 may be clamped into a circular hollow formed by engaging the first groove 641*a* and the second groove 642*a* to be rotatably seated and fixed.

The moving guide 650 may be formed as a coupling of the first body 610 and the second body 620 in a position opposite to the fixing guide.

The moving guide 650 may be formed between the first body 610 and the second body 620. Here, the moving guide 650 may be formed in a position opposite the fixing part, and be configured to guide the up and down movement of the moving protrusion part 633.

The moving guide 650 may include the guide protrusion 652 and a seating member 651.

The guide protrusion 652 may protrude toward the chamber 611 from the second extension groove 6213. In addition, an end of the guide protrusion 652 may be sharply formed so that it may be easily fitted corresponding to a fastening hole 6512 to be described later.

The seating member 651 may be provided to protrude in a first direction in an inlet groove 611*a* formed to be inserted into the other end of an inner peripheral surface of the chamber 611. The fastening hole 6512 may be formed in the seating member 651 so that the end of the guide protrusion 652 may be inserted.

When the second body 620 is seated above the first body 610, the end of the guide protrusion 652 may be inserted into and fixed to the fastening hole 6512.

As described above, the moving protrusion part 633 has a structure coupled to the moving guide 650. Here, the guide protrusion 652 passes through the guide hole 6332 formed at an end of the second protrusion 631 and is seated in the fastening hole 6512. Therefore, when the blocking body 631 is pushed downward by the pressure of the medical fluid, the guide hole 6332 may be guided to move upward and downward from one end of the second extension groove 6213 to the fastening hole 6512 along the guide protrusion 652 while being fitted in the guide protrusion 652.

Figure 25:
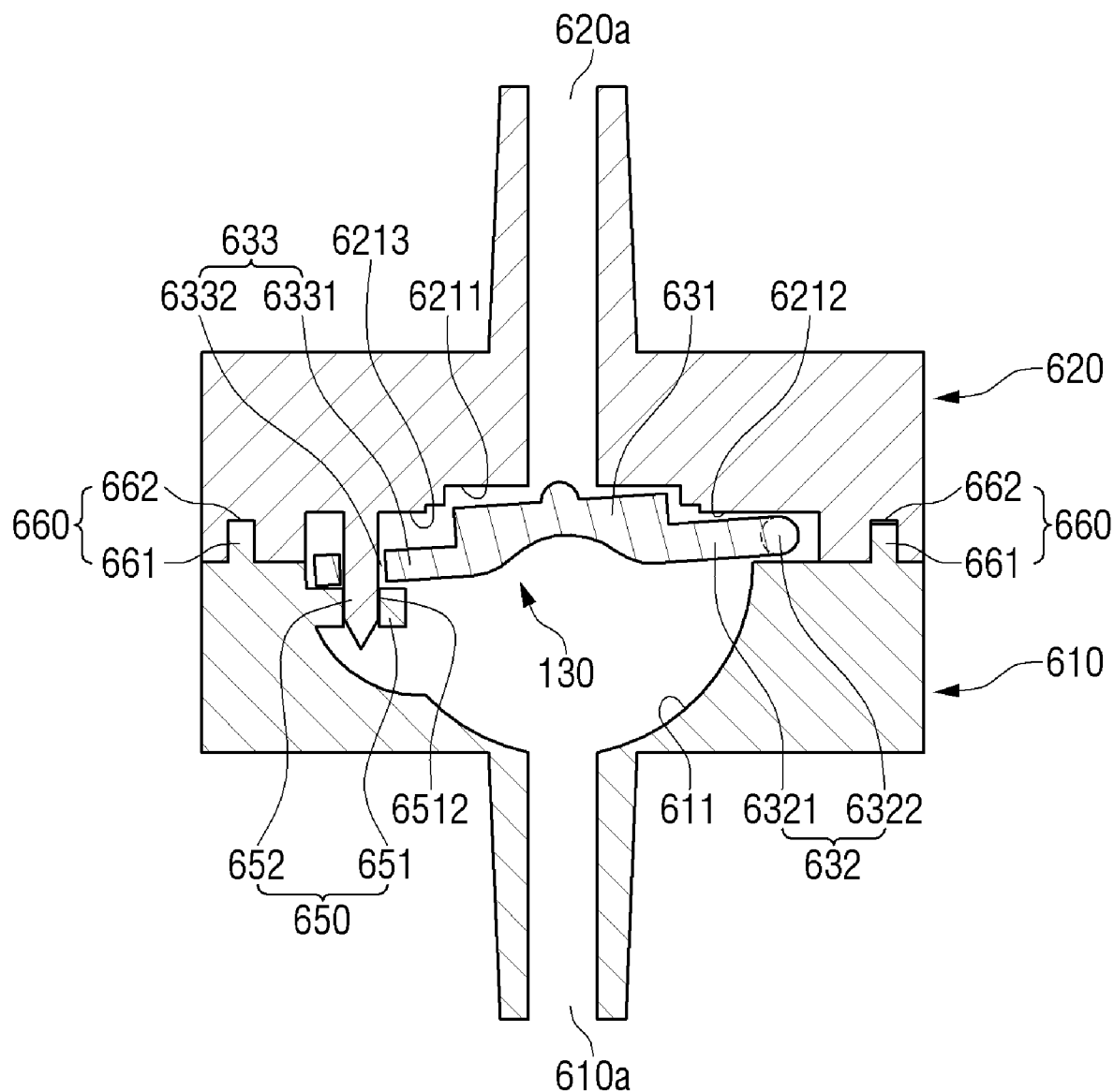
FIG. 25 is a view schematically showing a driving state of the apparatus for preventing the backflow according to the embodiment of the present invention.

FIG. 25 is a view schematically showing a driving state of the apparatus 600 for preventing the backflow according to the embodiment of the present invention.

Referring to FIG. 25, the backflow prevention member 630 may be positioned between the first body 610 and the second body 620. In addition, the backflow prevention member 630 may be fixedly coupled such that the backflow prevention member 630 may be driven like a plate spring according to the coupling of the first body 610 and the second body 620 in a state in which the backflow prevention member 630 is coupled to the first body 610 or the second body 620.

Specifically, when the backflow prevention member 630 is seated on the seating part 621, the blocking body 631 may be seated in the seating groove 6211, the fixing protrusion part 632 may be seated in the first extension groove 6212, and the moving protrusion part 633 may be seated in the second extension groove 6213. Accordingly, the rotation protrusion part 6322 may be positioned in the first fixing member 641 formed in the extension groove 6212a of the first protrusion part 6321, and the guide hole 6332 may be fitted into the guide protrusion 652.

As described above, when the second body 620 is placed on the first body 610 while the backflow prevention member 630 is seated on the second body 620, at one side between the first body 610 and the second body 620, the second fixing member 642 formed on one surface of the first body 610 is engaged with the first fixing member 641. Accordingly, the fixing protrusion part 632, specifically, the rotation protrusion part 6322 may be clamped to be rotatable.

In addition, at the other side between the first body 610 and the second body 620, the guide protrusion 652 is inserted and fixed to the seating member 651 formed in the inlet groove 611a to the other surface of the first body 610, specifically the fastening hole 6512. Accordingly, the rotation protrusion part 633 may be held so as to be movable in the up-and-down direction.

Accordingly, when the medical fluid is introduced through the inflow passage 620a, the blocking body 631 may be pushed by the pressure of the medical fluid, and the moving protrusion part 633, specifically, the fastening hole 6512 may be guided to move downward along the guide protrusion 652. As the inflow passage 620a is opened due to the downward movement of the blocking body 631, which was in close contact with the seating groove 6211 and blocking the inflow passage 620a, the medical fluid may be accommodated into the chamber 611 through the open space.

In addition, when the medical fluid flows back through the discharge passage 610a, the medical fluid flowing back into the discharge passage 610a may be instantaneously pressurized toward a pressing groove of the blocking body 631. Accordingly, the blocking body 631 is pushed from the lower side to the upper side, and the fastening hole 6512 positioned below the guide protrusion 652 rises along the guide protrusion 652. As the fastening hole 6512 rises, the blocking body 631 is in close contact with the seating groove 6211, and the inflow passage 620a is blocked. Accordingly, it is possible to block the inflow of the medical fluid flowing into the chamber 611 in the reverse direction toward the inflow passage 620a.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

What is claimed is:

1. An apparatus for preventing backflow, comprising:
a first body comprising a hemispherical chamber with an opened surface and comprising a discharge passage in a lower portion of the chamber;
a second body mounted on the opened surface of the first body, the second body comprising a seating part on a first surface facing the opened surface of the first body and comprising an inflow passage connected to the seating part; and
a disk-shaped backflow prevention member closely mounted to the seating part between the first body and the second body, the backflow prevention member opening or closing between the seating part and the chamber while moving about one end by a predetermined rotation according to a forward flow of a medical fluid flowing in the inflow passage and a backflow generated in the discharge passage, and
wherein the backflow prevention member comprises:
a blocking body closely coupled to the seating part;
a fixing protrusion part protruding from a first portion of the blocking body and rotatably seated and fixed between the opened surface of the first body and the first surface of the second body; and
a moving protrusion part protruding from a second portion of the blocking body and provided between the opened surface of the first body and the first surface of the second body, the moving protrusion part being guided to move in an up-and-down direction between the chamber and the seating part,
wherein a fixing part and a moving guide are formed between the first body and the second body,
wherein the fixing part is formed between the first body and the second body, and the fixing protrusion part is rotatably fixed on the fixing part, and
wherein the moving guide is formed between the first body and the second body, and the moving guide is configured to guide up-and-down movement of the moving protrusion part, and
wherein the moving protrusion part is movably coupled with the moving guide to move up and down, the fixing protrusion part is movably coupled to the fixing part as a fixed axis of rotation, and the backflow prevention member is moved up and down on the fixing part to open the seating part to the chamber and to close the seating part from the chamber.

2. The apparatus of claim 1, wherein the seating part comprises:
a seating groove in which the blocking body is seated in close contact, the seating groove having a diameter smaller than an upper portion of the chamber;
a first extension groove extending in a first direction from a first portion of the seating groove toward an outer peripheral surface of the second body, wherein the fixing protrusion part is seated in the first extension groove; and
a second extension groove extending in a second direction opposite to the first direction from a second portion of the seating groove, wherein the moving protrusion part is seated in the second extension groove.

3. The apparatus of claim 2, wherein the first extension groove and the second extension groove extend stepwise from the first portion and the second portion of the seating groove, respectively, toward the first body.

4. The apparatus of claim 2, wherein one surface of the blocking body is formed as a close contact surface that is in close contact with the seating groove, and
wherein an other surface of the blocking body is formed as a pressing surface having a pressing groove that is in contact with the medical fluid flowing back.

5. The apparatus of claim 2, wherein the fixing protrusion part comprises:
a first protrusion protruding from the blocking body in a first direction; and
a rotating protrusion formed in a cylindrical shape in a vertical direction around the first protrusion in an end of the first protrusion.

6. The apparatus of claim 5, wherein the first extension groove comprises:

an extension groove of the first protrusion extending in the first direction from the seating groove and in which the first protrusion is seated and is in close contacted; and an extension groove of the rotation protrusion extending in a direction perpendicular to the extension groove of the first protrusion, and in which the rotation protrusion is seated and rotatably fixed.

7. The apparatus of claim 6, wherein the moving protrusion part comprises:

a second protrusion protruding from the blocking body in a second direction opposite to the first direction; and a guide hole formed at an end of the second protrusion and guiding up-and-down movement of the second protrusion.

8. The apparatus of claim 7, wherein the fixing part comprising a first fixing member positioned on the opened surface of the first body around the chamber and forming a semi-hollow-shaped second first groove and a second fixing member positioned in the extension groove of the rotation protrusion and forming a semi-hollow-shaped second groove corresponding to the semi-hollow-shaped first groove of the first fixing member, such that the fixing part rotatably fixes the fixing protrusion part in a circular hollow formed by engaging the first groove and the second groove; and wherein the moving guide comprising a guide protrusion protruding from the second extension groove toward the chamber and a seating member protruding in the first direction into an inlet groove inserted to an end of an inner peripheral surface of the chamber so as to guide the up-and-down movement of the moving protrusion part, wherein a fastening hole into which an end of the guide protrusion is inserted is formed in the seating member.

* * * * *